US010709338B2

(12) United States Patent
Arai et al.

(10) Patent No.: US 10,709,338 B2
(45) Date of Patent: Jul. 14, 2020

(54) USEFUL INFORMATION PRESENTATION DEVICE

(71) Applicants: DAIKIN INDUSTRIES, LTD., Osaka-shi, Osaka (JP); TOKYO INSTITUTE OF TECHNOLOGY, Meguro-ku, Tokyo (JP)

(72) Inventors: Junichiro Arai, Osaka (JP); Takashi Gotou, Osaka (JP); Makoto Iwakame, Osaka (JP); Kenichi Hino, Osaka (JP); Tomoya Hirano, Osaka (JP); Yasunori Kotani, Tokyo (JP); Yoshimi Ohgami, Tokyo (JP); Taro Tomatsu, Tokyo (JP)

(73) Assignees: Daikin Industries, Ltd., Osaka (JP); Tokyo Institute of Technology, Tokyo (JP)

( * ) Notice: Subject to any disclaimer, the term of this patent is extended or adjusted under 35 U.S.C. 154(b) by 166 days.

(21) Appl. No.: 15/767,067

(22) PCT Filed: Oct. 17, 2016

(86) PCT No.: PCT/JP2016/080711
§ 371 (c)(1),
(2) Date: Apr. 9, 2018

(87) PCT Pub. No.: WO2017/065313
PCT Pub. Date: Apr. 20, 2017

(65) Prior Publication Data
US 2018/0289266 A1 Oct. 11, 2018

(30) Foreign Application Priority Data

Oct. 15, 2015 (JP) ................................ 2015-203357
Oct. 15, 2015 (JP) ................................ 2015-203358
Oct. 15, 2015 (JP) ................................ 2015-203359

(51) Int. Cl.
A61B 5/01 (2006.01)
A61B 5/00 (2006.01)
A61B 5/026 (2006.01)
A61B 5/11 (2006.01)
A61B 5/16 (2006.01)

(52) U.S. Cl.
CPC ................. *A61B 5/01* (2013.01); *A61B 5/00* (2013.01); *A61B 5/0261* (2013.01);
(Continued)

(58) Field of Classification Search
CPC .. A61B 5/01; A61B 5/00; A61B 5/441; A61B 5/165; A61B 5/1118; A61B 5/0261; A61B 5/16
See application file for complete search history.

(56) References Cited

U.S. PATENT DOCUMENTS

2014/0121540 A1   5/2014 Raskin
2017/0281070 A1  10/2017 Arai et al.

FOREIGN PATENT DOCUMENTS

JP    2013-176406 A   9/2013
WO    2016/035719 A1  3/2016

OTHER PUBLICATIONS

European Search Report of corresponding EP patent Application No. 16 85 5564.7 dated Mar. 25, 2019.
(Continued)

*Primary Examiner* — Mark Bockelman
(74) *Attorney, Agent, or Firm* — Global IP Counselors, LLP

(57) ABSTRACT

A useful information presentation device includes a facial skin temperature acquisition unit and/or a blood circulation volume acquisition unit, a brain activity estimation unit, and a useful information presentation unit. The facial skin temperature acquisition unit acquires facial skin temperature data in time-series. The blood circulation volume acquisition unit acquires photographic image data by imaging the facial
(Continued)

surface in time-series. The brain activity estimation unit decomposes the facial skin temperature data and/or the facial blood circulation volume data into a plurality of components by singular value decomposition, principal component analysis, or independent component analysis, and the brain activity estimation unit estimating brain activity of the subject based on the plurality of components. The useful information presentation unit presents, to the subject, useful information related to an emotional or physical state based on the brain activity of the subject estimated by the brain activity estimation unit.

13 Claims, 26 Drawing Sheets

(52) U.S. Cl.
CPC ............ *A61B 5/1118* (2013.01); *A61B 5/165* (2013.01); *A61B 5/441* (2013.01)

(56) References Cited

OTHER PUBLICATIONS

International Preliminary Report of corresponding PCT Application No. PCT/JP2016/080711 dated Apr. 26, 2018.
International Search Report of corresponding PCT Application No. PCT/JP2016/080711 dated Jan. 17, 2017.

FIG. 26

| Pattern No. | Changes by time frame in estimation results of brain activity | Useful information (advice) | Notes | | |
|---|---|---|---|---|---|
| | | | Changes in brain activity | Changes in autonomic nervous system | Changes in skin temperature |
| 1 | Brain activity is low in the morning, the amount of brain activity rises as morning transitions to afternoon, and the amount of brain activity decreases as afternoon transitions to evening | Normal: Rhythm is maintained by your lifestyle | Balance achieved between number of daily increases and decreases in brain activity | Rhythm achieved in which subject is relaxed in the morning, becomes excited during the day, and becomes relaxed again at night | Low in the morning, rises during the day, and decreases in the evening |
| 2 | Brain activity is high from the morning and the amount of brain activity is constant until night | Abnormal: Overwork, etc. has resulted in a state of excitement. Get some sleep or take a break and let your body rest. | Number of daily increases in brain activity is elevated | Excited state continues all day | High to start and does not decrease, even in the evening |
| 3 | The amount of brain activity is constant at a low level of brain activity | Abnormal: Physical activity has decreased and "you are in a slump". Become physically active through light exercise, going outside, etc. | Number of daily increases in brain activity is low | Period decreased autonomic nervous system activity continues for a long period of time | Low to start and does not rise during the day |

205

USEFUL INFORMATION PRESENTATION DEVICE

CROSS-REFERENCE TO RELATED APPLICATIONS

This U.S. National stage application claims priority under 35 U.S.C. § 119(a) to Japanese Patent Application Nos. 2015-203357, filed in Japan on Oct. 15, 2015, 2015-203358, filed in Japan on Oct. 15, 2015, and 2015-203359, filed in Japan on Oct. 15, 2015, the entire contents of which are hereby incorporated herein by reference.

TECHNICAL FIELD

The present invention relates to a useful information presentation device.

BACKGROUND ART

In the prior art, data detected by electroencephalography (EEG), functional magnetic resonance imaging (fMRI), and near infrared spectroscopy (NIRS) has been used for human health management. An example thereof is the technology described in Japanese Unexamined Patent Application Publication No. 2013-176406.

SUMMARY

Technical Problems

However, there are problems with these methods. For example, preparation work such as pretreating the electrodes before application to the subject is complicated, measuring must be carried out in a prescribed measurement room, and tremendous costs are involved. These problems has led a situation in which useful information related to emotional and physical states cannot be obtained easily.

An object of the present invention is to provide a useful information presentation device whereby useful information related to health management can be easily obtained.

Solutions to the Problems

A useful information presentation device according to a first aspect of the present invention includes facial skin temperature acquisition means and/or facial blood circulation volume acquisition means, brain activity estimation means, and useful information presentation means. The facial skin temperature acquisition means acquire facial skin temperature data in time-series. The facial skin temperature data includes skin temperature data detected from the facial surface of the subject and position data of the detection site of the skin temperature data. The facial blood circulation volume acquisition means acquire facial blood circulation volume data in time-series. Photographic image data of the facial surface of the subject is captured in time-series and subjected to RGB processing. The facial blood circulation volume data is acquired on the basis of RGB data, of the photographic image data, obtained from the RGB processing. A plurality of components is obtained by decomposing the facial skin temperature data and/or the facial blood circulation volume data by singular value decomposition, principal component analysis, or independent component analysis. The brain activity estimation means estimate the brain activity of the subject on the basis of this plurality of components. The useful information presentation means present useful information related to an emotional or physical state on the basis of the brain activity of the subject estimated by the brain activity estimation means.

With the useful information presentation device according to the first aspect of the present invention, the brain activity of the subject is estimated on the basis of the time-series facial skin temperature data and/or facial blood circulation volume data acquired by the facial skin temperature acquisition means and/or the facial blood circulation volume acquisition means. As such, with this useful information presentation device, the brain activity of the subject can be estimated without using electroencephalogram electrodes or other sensors that require pretreatment before being applied. As a result, the subject can easily obtain useful information related to the emotional and physical state.

A useful information presentation device according to a second aspect of the present invention is the useful information presentation device of the first aspect, wherein the brain activity estimation means extract, from the plurality of components, a component having a waveform with an amplitude that has correlation with changes of a brain activated time and a brain resting time as a determination component. Additionally, the brain activity estimation means estimate the brain activity of the subject on the basis of the determination component. With this useful information presentation device, a component having correlation with the brain activated time/resting time is extracted from the plurality of components as a determination component for estimating the brain activity of the subject. As such, it is possible to estimate brain activity from a component presumed to be highly related to the brain activity of the subject. As a result, the validity of the useful information can be enhanced.

A useful information presentation device according to a third aspect of the present invention is the useful information presentation device of the first or second aspect, wherein the facial skin temperature data acquisition means and/or the facial blood circulation volume acquisition means acquire at least the facial skin temperature data and/or the facial blood circulation volume data of the forehead and/or the area around the paranasal sinuses of the subject.

The brain has a mechanism called the selective brain cooling system whereby the brain is cooled independently of body temperature. The selective brain cooling system is known to discharge heat generated by brain activity using the areas around the forehead and the paranasal sinuses. Additionally, the facial skin temperature is thought to be proportional to the facial blood circulation volume.

With the useful information presentation device according to the third aspect of the present invention, the brain activity of the subject is estimated on the basis of the time-series facial skin temperature data and/or facial blood circulation volume data of the forehead and/or the area around the paranasal sinuses, which is presumed to reflect brain activity. As such, with this useful information presentation device, the brain activity of the subject can be accurately estimated. As a result, the validity of the useful information can be enhanced.

A useful information presentation device according to a fourth aspect of the present invention is the useful information presentation device of any one of the first to third aspects, wherein the facial skin temperature data acquisition means and/or the facial blood circulation volume acquisition means, and the useful information presentation means are housed in a smart device.

With the useful information presentation device according to the fourth aspect of the present invention, information is input and output by the smart device and, as such, the subject can easily obtain useful information related to health management. Additionally, by providing the brain activity estimation means on a server, the calculation load can be reduced.

A useful information presentation device according to a fifth aspect of the present invention is the useful information presentation device of any one of the first to fourth aspects, wherein the facial skin temperature data acquisition means and/or the facial blood circulation volume acquisition means, the brain activity estimation means, and brain age presentation means are housed in a smart device.

With the useful information presentation device according to the fifth aspect of the present invention, information is input and output and calculations are performed by the smart device. As a result, the subject can easily obtain useful information related to the emotional or physical state.

A useful information presentation device according to a sixth aspect of the present invention is the useful information presentation device according to any one of the first to fifth aspects, further including an emotion storage unit. The estimation results of brain activity and emotion data indicating an emotion of a human are associated with one another and stored in the emotion storage unit. The brain activity estimation means calculate the estimation results of brain activity. The useful information presentation means extract, from the emotion storage unit, emotional data of the subject on the basis of the estimation results, and present the emotional data.

With the useful information presentation device according to the sixth aspect of the present invention, the estimation results of brain activity and the emotion data indicating an emotion of a human are associated with one another and stored in the emotion storage unit. As such, correlation between brain activity and emotions can be consecutively optimized.

A useful information presentation device according to a seventh aspect of the present invention is the useful information presentation device according to the sixth aspect, wherein an infant is the subject of the useful information presentation device. In this case, an estimation value of brain activity and infant emotion data indicating an emotion of an infant are associated with one another and stored in the emotion storage unit.

With the useful information presentation device according to the seventh aspect of the present invention, the estimation results of brain activity and the infant emotion data indicating an emotion of the infant are associated with one another and stored in the emotion storage unit. As such, correlation, specialized for infants, between brain activity and emotions can be used.

A useful information presentation device according to an eighth aspect of the present invention is the useful information presentation device according to the sixth or seventh aspect, wherein, an emotion of a non-human animal, instead of a human, is determined. As a result, the emotions of a companion animal (pet) or the like can be easily determined.

A useful information presentation device according to a ninth aspect of the present invention is the useful information presentation device according to any one of the first to fifth aspects, further including a brain age storage unit. In this case, the estimation results of brain activity and brain age data indicating brain age are associated with one another and stored in the brain age storage unit. The brain activity estimation means calculate the estimation results of brain activity. The useful information presentation means extract, from the brain age storage unit, brain age data of the subject on the basis of the estimation results, and present the brain age data.

With the useful information presentation device according to the ninth aspect of the present invention, the estimation results of brain activity and the brain age data indicating brain age are associated with one another and stored in the brain age storage unit. As such, correlation between brain activity and brain age can be consecutively optimized.

A useful information presentation device according to a tenth aspect of the present invention is the useful information presentation device of any one of the first to fifth, and ninth aspects, wherein the facial skin temperature data acquisition means and/or the facial blood circulation volume acquisition means are installed in a gaming machine. In this case, the facial skin temperature data acquisition means and/or the facial blood circulation volume acquisition means acquire the facial skin temperature data in time-series and/or the facial blood circulation volume data for a predetermined period of time after a game start by the gaming machine.

With the useful information presentation device according to the tenth aspect of the present invention, the configuration described above is provided and, as a result, the brain age can be presented during game running Additionally, by constituting the brain function activation task from the game being run by the gaming machine, the brain age can be presented by running the game.

A useful information presentation device according to an eleventh aspect of the present invention is the useful information presentation device according to any one of the first to fifth aspects, further including a useful information storage unit. The estimation results of brain activity and the useful information related to health management are associated with one another and stored in the useful information storage unit. The brain activity estimation means calculate the estimation results of brain activity. The useful information presentation means extract, from the useful information storage unit, useful information for the subject on the basis of the estimation results, and present the useful information.

With the useful information presentation device according to the eleventh aspect of the present invention, the estimation results of brain activity and the useful information related to health are associated with one another and stored in the useful information storage unit. As such, correlation between brain activity and useful information can be consecutively optimized.

A useful information presentation device according to a twelfth aspect of the present invention is the useful information presentation device according to the eleventh aspect, wherein changes by time frame in the estimation results of brain activity are associated with the useful information and stored in the useful information storage unit. In this case, the facial skin temperature data acquisition means and/or the facial blood circulation volume acquisition means associate and acquire the facial skin temperature data and/or the facial blood circulation volume data with time information. The brain activity estimation means calculate the estimation results of brain activity in association with the time information. The useful information presentation means extract, from the useful information storage unit, the useful information in accordance with the changes by time frame in the estimation results of brain activity on the basis of the estimation results and the time information, and present the useful information to the subject.

With the useful information presentation device according to the twelfth aspect of the present invention, the useful information corresponding to the changes by time frame in the estimation results of brain activity is extracted and presented to the subject. As such, useful information corresponding to a circadian rhythm can be presented.

A useful information presentation device according to a thirteenth aspect of the present invention is the useful information presentation device of any one of the first to fifth, eleventh, and twelfth aspects, wherein the facial skin temperature data acquisition means and/or the facial blood circulation volume acquisition means are disposed behind a mirror member.

With the useful information presentation device according to the thirteenth aspect of the present invention, the facial skin temperature data and/or photographic image data can be acquired and useful information is presented each time the subject uses the mirror. As a result, user convenience can be enhanced.

A useful information presentation device according to a fourteenth aspect of the present invention is the useful information presentation device of the fourth or fifth aspect, wherein the smart device includes mirrorizing means that mirrorize a display unit of the smart device, and the facial skin temperature data acquisition means and/or the facial blood circulation volume acquisition means are disposed behind the display unit of the smart device.

With the useful information presentation device according to the fourteenth aspect of the present invention, the facial skin temperature data and/or photographic image data can be acquired and useful information is presented each time the subject uses the mirrorized display unit of the smart device. As a result, user convenience can be enhanced.

Advantageous Effects of Invention

With the useful information presentation device according to the first aspect of the present invention, useful information related to the emotional or physical state can be easily presented.

With the useful information presentation device according to the second and third aspects of the present invention, the validity of the useful information can be enhanced.

With the useful information presentation device according to the fourth and fifth aspects, a smart device can be used to easily present useful information.

With the useful information presentation device according to the sixth aspect of the present invention, correlation between brain activity and emotions can be consecutively optimized.

With the useful information presentation device according to the seventh aspect of the present invention, correlation between brain activity and emotions, which is specialized for infants, can be used.

With the useful information presentation device according to the eighth aspect of the present invention, the emotions of a companion animal (pet) or the like can be easily determined.

With the useful information presentation device according to the ninth aspect of the present invention, correlation between brain activity and brain age can be consecutively optimized.

With the useful information presentation device according to the tenth aspect of the present invention, the brain age can be presented during game running.

With the useful information presentation device according to the eleventh aspect of the present invention, correlation between brain activity and brain age can be consecutively optimized.

With the useful information presentation device according to the twelfth aspect of the present invention, useful information corresponding to a circadian rhythm can be presented.

With the useful information presentation device according to the thirteenth aspect of the present invention, user convenience can be enhanced.

With the useful information presentation device according to the fourteenth aspect of the present invention, user convenience can be enhanced.

BRIEF DESCRIPTION OF THE DRAWINGS

FIG. 26 is a schematic drawing of a useful information storage unit according to an embodiment of the present invention.

DESCRIPTION OF EMBODIMENTS

Figure 1B:
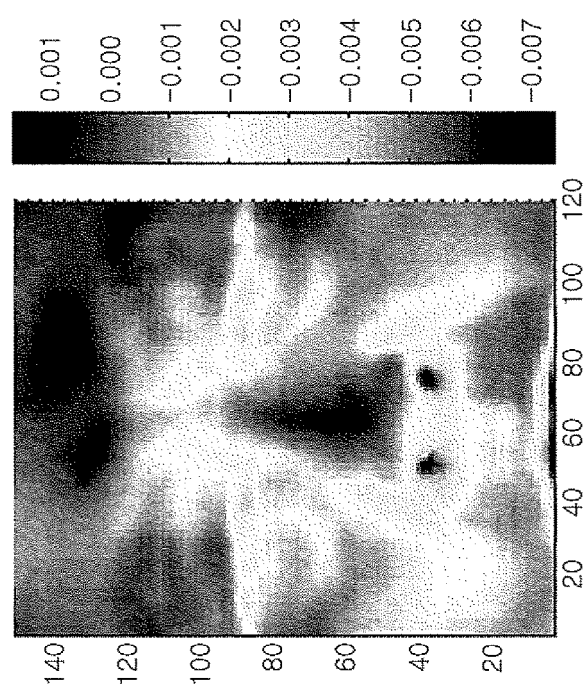
FIGS. 1A and 1B illustrate an example of photographic image data and the results of analyzing the same.

Before describing the embodiments of the present invention, the findings made by the inventors that served as an important foundation for the inventors to contrive the present invention will be described.

(1) Summary of Findings Made by the Inventors

It is known that human intellectual activity (cognitive activity and the like) and emotional activity (activity such as pleasure/displeasure) are reflected in human brain activity. Attempts to estimate human brain activity have been made in the past, but in most cases, the attempts involved using data detected by electroencephalography, functional magnetic resonance imaging, and/or near infrared spectroscopy.

In cases where, for example, electroencephalography is adopted as the detection method, it is necessary to attach brain wave electrodes to the subject. Additionally, resistance that occurs between the skin and the electrodes when the brain wave electrodes are attached must be reduced. Consequently, a procedure such as a process to abrade the skin or an application of a paste to the electrodes needs to be carried out. In cases where functional magnetic resonance imaging is adopted, there are restrictions on measurement conditions, such as the impossibility of measurement at any location other than an MRI room and the inability to bring metal into the measurement room. In cases where near infrared spectroscopy is adopted, a probe needs to be attached to the subject. However, wearing the probe for a long time can be painful to the subject and, in some cases, due to the contact state between the hair of the subject and the probe, the detections by the probe may not be accurate. Thus, when using conventional detection methods to measure human brain activity, a significant burden is imposed on the subject, specifically, pretreatment is needed to attach the brain wave electrodes, probes, etc., and/or the measurement conditions are limited.

Accordingly, there is a need to develop an approach whereby the burden on the subject can be reduced and also whereby human brain activity can be easily estimated.

The inventors postulated that it might be possible to estimate human brain activity on the basis of human facial skin temperature or the state of facial blood circulation, which is thought to be proportional to the facial skin temperature. Human facial skin temperature can be acquired using a measurement device such as a thermography device. The state of facial blood circulation, that is, facial blood circulation volume can be estimated from RGB data of photographic images of the facial surface, which is obtained using an imaging device. The facial skin temperature and/or photographic images of the facial surface can be acquired without using electroencephalogram electrodes, probes, or other sensors that require pretreatment before being applied.

However, it is known that human facial skin temperature changes under the influence of various factors such as outside air temperature and/or autonomic nervous activity. As such, when attempting to estimate brain activity on the basis of the facial skin temperature or on the basis of the facial blood circulation volume, which is thought to be proportional to the facial skin temperature, it is very difficult to determine whether only brain activity is reflected in the acquired data.

After much research, the present inventors discovered that it is possible to identify a component indicating a change in the facial skin temperature or a change in the facial blood circulation volume in brain activity by: detecting the facial skin temperature; decomposing, into a plurality of components, time-series facial skin temperature data including the detected temperature data and position data (coordinate data) of the detection site, or decomposing, into a plurality of components, time-series facial blood circulation volume data calculated on the basis of RGB data obtained from time-series photographic image data of the facial surface, by singular value decomposition, principal component analysis, or independent component analysis; and analyzing the plurality of the decomposed components. Thus, the present inventors conceived the present invention, in which the brain activity of the subject is estimated and analyzed, thereby enabling the visualization of the physiological state of the subject on the basis of the estimated brain activity.

(2) Acquisition Method of Various Facial Data and Analysis Method of Acquired Various Facial Data (2-1) Acquisition Method of Facial Skin Temperature Data and Analysis Method of Facial Skin Temperature Data Next, a description is given of an acquisition method of facial skin temperature data and analysis method of facial skin temperature data used by the present inventors to reach the findings described above.

In this test, facial skin temperature data was acquired from six subjects. Specifically, each subject was seated in a chair placed in an artificial climate room maintained at a room temperature of 25° C., and facial skin temperature data was acquired from the entire facial surface of the subject using an infrared thermography device. The infrared thermography device was capable of detecting infrared radiant energy emitted from the subject using an infrared camera, converting the detected infrared radiant energy to a facial temperature (herein, the temperature in Celsius) of the subject, and displaying and/or storing a temperature distribution thereof as facial skin temperature data (e.g. image data representing the temperature distribution). In this test, an R300 (manufactured by NEC Avio Infrared Technologies Co., Ltd.) was used as the infrared thermography device. The infrared camera was set in front of the subject at a position 1.5 m away from the subject. The facial skin temperature data was acquired for 30 minutes.

Additionally, in this test, brain function activation tasks were given to the subjects while the facial skin temperature data was being acquired. Thus, facial skin temperature data during brain resting time and facial skin temperature data during brain activated time were acquired. The brain function activation tasks were presented to the subjects as images on a display device or the like. Examples thereof included calculation, recognition of numbers, shapes, and colors, memorization of symbols, letters, and language, and other psychological tasks. In this test, mental multiplication was used as the brain function activation task. The subjects were instructed to multiply numbers displayed in longhand on the display device, and input answers using a keyboard. In this test, the brain function activation tasks were continuously given to the subjects for ten minutes after five minutes had elapsed since the start of acquiring the facial skin temperature data.

To analyze the facial skin temperature data, the acquired facial skin temperature data was subjected to singular value decomposition. Here, Singular Value Decomposition (SVD) of MATLAB (registered trademark) was used as the analysis tool. In the singular value decomposition, the target was set as all of the time-series facial skin temperature data acquired (30-minutes of data), the factor was set as time data every of 30 seconds (60 time points for 30 minutes), and the measure was set as the facial skin temperature data (240×320 pixels) during each period (the 30 seconds). The facial skin temperature data X was decomposed into a plurality of components by singular value decomposition. Then, for each component, a time distribution V, a space distribution U, and a singular value S representing the magnitude of the component were calculated. The relationships between these values is expressed in the following equation. Note that V' is a matrix obtained by interchanging the columns and rows of V.

$$X=(U*S)*V'$$ Equation 1

Then, the time distribution V and the space distribution U of each component resulting from the singular value decomposition were plotted on graphs to create a component waveform diagram and a temperature distribution diagram for each component.

Furthermore, the component waveform diagram and the temperature distribution diagram for each component were analyzed to identify a component indicating a change in skin temperature that reflects brain activity.

The component waveform diagram for each component was analyzed to determine the presence/absence of correlation between the amplitude of the component waveform and each of the brain resting time and the brain activated time. Specifically, evaluations were conducted as to whether or not correlation existed between the amplitude shown in the component waveform diagram for each component and the brain resting time period/brain activated time period. In this test, during the period of acquiring the facial skin temperature data, the brain resting time was defined as a period of five minutes from the start of data acquisition and a period of 15 minutes from a point in time after 15 minutes had elapsed since the start point of data acquisition to the end of data acquisition. These were periods in which the brain function activation task was not given to the subjects. Additionally, the brain activated time was defined as a period of 10-minutes from a point in time occurring after five minutes had elapsed since the start of data acquisition, up to a point in time after 10 minutes had elapsed. This was a period in which the brain function activation task was being given to the subjects. Then, evaluations were conducted to determine the presence/absence of correlation between the amplitude shown in the component waveform diagram for each component and each of the brain resting time and the brain activated time. Note that statistical correlation analysis was performed to determine the presence/absence of correlation. When the significance level ($\alpha$) was 0.05 or lower, it was determined that correlation existed.

The temperature distribution diagram for each component was analyzed to determine the presence/absence of temperature changes at a predetermined site on the facial surface. The brain has a mechanism called the selective brain cooling system whereby the brain is cooled independently of body temperature. The selective brain cooling system is known to discharge heat generated by brain activity using the forehead and the area around the paranasal sinuses (including the area between the eyebrows and the area around the nose). As such, in this test, the temperature distribution diagram for each component was evaluated to determine the presence/absence of temperature changes at the forehead and the area around the paranasal sinuses. Note that, in the temperature distribution diagrams, the presence/absence of temperature changes at the forehead and the area around the paranasal sinuses was evaluated on the basis of visual inspection, or on the basis of whether or not the temperatures of the forehead and the area around the paranasal sinuses differed one standard deviation (SD) or more from the average temperature of all measurement data of the temperatures of the forehead and the area around the paranasal sinuses.

Additionally, polarity (positive or negative) of the facial skin temperature data X is determined by the relationships between the values of the space distribution U, the singular value S, and the time distribution V. As such, in some cases, polarity may appear inverted in the temperature distribution diagram and the component waveform diagram for each component. Therefore, polarity was not considered when evaluating the component waveform diagrams and the temperature distribution diagrams.

As described above, in this case, the infrared thermography device converts the infrared radiant energy detected from the subject into temperatures, and uses the temperature distribution thereof as the facial skin temperature data. However, when acquiring the facial skin temperature of a human subject using the infrared thermography device, various temperature changes unrelated to brain activity (i.e. noise), such as facial movements and/or autonomic nervous activity, are also acquired as the facial skin temperature data. Therefore, in order to detect such temperature changes that are unrelated to brain activity, relative facial skin temperature data was created for which an average of all of the temperature data included in the facial skin temperature data every 30 seconds is set to 0, the created facial skin temperature data was also subjected to singular value decomposition in which the SVD of MATLAB (registered trademark) is used as the analysis tool, a component waveform diagram and a temperature distribution diagram for each component were created in accordance with the singular value S, and the diagrams were analyzed to identify a component indicating a change in skin temperature that reflects brain activity.

For the sake of convenience, in the following description, the facial skin temperature data, acquired by the infrared thermography device, is referred to as "facial skin temperature data based on temperature conversion data"; and the relative facial skin temperature data, for which the average of all of the temperature data included in the facial skin temperature data based on temperature conversion data obtained every predetermined time period (every 30 seconds in this test) is set to "0", is referred to as "facial skin temperature data based on relative temperature conversion data."

Additionally, for one of the six subjects, in addition to detecting the facial skin temperature using the infrared thermography device, electrodes were connected to the scalp of the subject and electroencephalograms were taken. An evaluation was conducted for correlation between the amplitude of the component waveform diagram and the amplitude of the β wave, which is known as a waveform that appears when awake or when the consciousness is nervous (brain wave in the 14 to 30 Hz frequency range). Note that, when taking the electroencephalogram, the electrodes were arranged at six sites (F3, F4, C3, C4, Cz, and Pz) specified by the International 10-20 System.

It can be expected that the head of the subject may move vertically while the brain function activation task is given to the subject. If such movement occurs, the position of the face of the subject with respect to the infrared camera will change. Therefore, a control test was conducted on one subject in order to verify whether such changes in the position of the face influence the changes in skin temperature. In the control test to verify the influence of movement of the subject when acquiring the facial skin temperature data, the same infrared thermography device used in the test described above was used to acquire the facial skin temperature data of the subject. However, in this case, the subject was instructed also to operate the keyboard at random timings during the period in which the brain function activation task was not given (that is, during brain resting time). The facial skin temperature data based on temperature conversion data and the facial skin temperature data based on relative temperature conversion data acquired by the control test were also subjected to singular value decomposition in which the SVD of MATLAB (registered trademark) was used as the analysis tool, a component waveform diagram and a temperature distribution diagram for each component were created in accordance with the singular value S, and the diagrams were analyzed to identify a component indicating a change in skin temperature that reflects brain activity.

Figure 1A:
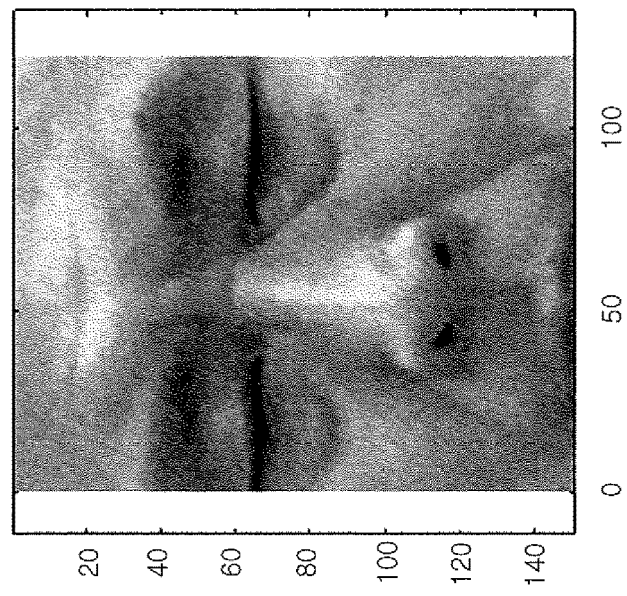

(2-2) Acquisition Method of Photographic Image Data of Facial Surface and Analysis Method of Photographic Image Data of Facial Surface FIG. 1A illustrates an example of photographic image data, captured using the imaging device, of the area around the paranasal sinuses of the facial surface of a subject. FIG. 1B illustrates an example of a blood circulation volume distribution diagram (image map).

Next, a description is given of an acquisition method of photographic image data of the facial surface and an analysis method of photographic image data of the facial surface used by the present inventors to reach the findings described above.

In this test, photographic image data of the facial surface was acquired from six subjects. Specifically, each subject was seated in a chair placed in an artificial climate room maintained at a room temperature of 25° C., and photographic image data of the area around the paranasal sinuses of the entire facial surface of the subject was acquired in time-series using an imaging device capable of chronologically acquiring images.

Additionally, based on the selective brain cooling system described above, it is postulated that changes in the facial blood circulation volume, thought to be proportional to the facial skin temperature resulting from brain activity, will appear at the forehead and/or the area around the paranasal sinuses. As such, the present inventors postulated that, if the changes in the facial blood circulation volume at least at the forehead and/or the area around the paranasal sinuses could be captured, it would be possible to accurately estimate brain activity. Therefore, in this test, photographic image data of the area around the paranasal sinuses of the facial surfaces of the subjects were acquired in time-series.

Additionally, in this test, an imaging device on the liquid crystal screen side of an iPad Air (registered trademark, manufactured by Apple) was used as the imaging device, and color video data was acquired as the time-series photographic image data. This imaging device was set in front of the subject at a position 1.0 m away from the subject. Then, using the imaging device, photographic image data was continuously captured for 30 minutes at an imaging period of 30 frames/second along the time axis. Thus, video data of the facial surface was acquired.

Furthermore, in this test, the brain function activation task was given to the subjects while the video data of the facial surface was being acquired. Thus, video data of the facial surface during brain resting time and video data of the facial surface during brain activated time were acquired. In this test, as in the test described above, "mental multiplication" was used as the brain function activation task. The subjects were instructed to multiply numbers displayed in longhand on the display device, and input answers using a keyboard. However, in this test, the brain function activation tasks were continuously given to the subjects for ten minutes after five minutes had elapsed since the start of acquiring the video data of the facial surface.

To analyze the video data of the facial surface, blood circulation volume data was calculated on the basis of RGB data obtained from the captured video data of the facial surface, and the calculated time-series blood circulation volume data was subjected to singular value decomposition, in which SVD of MATLAB (registered trademark) was used as the analysis tool. Here, in accordance with the CIE-L*a*b* color system, an erythema index a* that correlates with skin redness and hemoglobin amount was calculated from the RGB data of the image, and this erythema index a* was used as the blood circulation volume data. In the singular value decomposition, the target was set as the blood circulation volume data (the erythema index in this case) based on the RGB data acquired from all of the chronologically acquired video data (30 minutes of data), the factor was set as time data of every 30 seconds (60 time points for 30 minutes), and the measure was set as the erythema index calculated from the RGB data for each period (every 30 seconds) (the erythema index obtained by extracting frame data of one second every 30 seconds, and calculating on the basis of the average value of the RGB values obtained from the frame data; 240×320 pixels). The time-series blood circulation volume data based on the RGB data obtained from the video data of the facial surface was decomposed into a plurality of components by singular value decomposition. Then, for each component, a time distribution V, a space distribution U, and a singular value S representing the magnitude of the component was calculated. The relationships between these values are the same as those expressed in Equation 1 above.

Then, the time distribution V and the space distribution U of each component resulting from the singular value decomposition were plotted on graphs to create a component waveform diagram and a blood circulation volume distribution diagram for each component.

Furthermore, the component waveform diagram and blood circulation volume distribution diagram for each component were analyzed to identify a component indicating a change in the facial blood circulation volume, that is, an RGB change in the facial surface, that reflects brain activity.

The component waveform diagram for each component was analyzed to determine the presence/absence of correlation between the amplitude of the component waveform and each of the brain resting time and the brain activated time. Specifically, evaluations were conducted as to whether or not correlation existed between the amplitude shown in the component waveform diagram for each component and the brain resting time period/brain activated time period. In this test, during the period of acquiring the photographic image data of the facial surface, the brain resting time was defined as a period of five minutes from the start of data acquisition and a period of 15 minutes from a point in time after 15 minutes had elapsed since the start point of data acquisition to the end of data acquisition. These were periods in which the brain function activation task was not given to the subjects. Additionally, the brain activated time was defined as a period of 10-minutes from a point in time occurring after five minutes had elapsed since the start of data acquisition, up to a point in time after 10 minutes had elapsed. This was a period in which the brain function activation task was being given to the subjects. Then, evaluations were conducted to determine the presence/absence of correlation between the amplitude shown in the component waveform for each component and each of the brain resting time and the brain activated time. Note that statistical correlation analysis was performed to determine the presence/absence of correlation. When the significance level ($\alpha$) was 0.01 or lower, it was determined that correlation existed.

The blood circulation volume distribution diagram for each component was analyzed to determine the presence/absence of blood circulation volume changes at a predetermined site on the facial surface. The blood circulation volume distribution diagrams were created by arranging the space distributions U, calculated by pixel, at the respective positions of the pixels. The blood circulation volume distribution diagram for each component thus created was evaluated to determine the presence/absence of changes in blood circulation volume at the forehead and the area around the paranasal sinuses. Note that, in the blood circulation volume distribution diagrams, the presence/absence of a change in blood circulation volume at the forehead and the area around the paranasal sinuses was evaluated on the basis of the presence/absence of the change in the blood circulation volume that was observed through visual inspection, or on the basis of the value of the blood circulation volume at the forehead and the area around the paranasal sinuses as shown FIG. 1B was not "0.000".

Additionally, polarity (positive or negative) of the blood circulation volume data X was determined by the relationships between the values of the space distribution U, the singular value S, and the time distribution V. As such, in some cases, polarity may appear inverted in the blood circulation volume distribution diagram and the component waveform diagram for each component. Therefore, polarity was not considered when evaluating the component waveform diagrams and the blood circulation volume distribution diagrams.

Furthermore, in order to validate the correlation between the facial skin temperature and the facial blood circulation volume, while the photographic image data of the facial surfaces of the six subjects was being chronologically acquired, the facial skin temperature data was chronologically acquired using the infrared thermography device, the acquired facial skin temperature data was subjected to singular value decomposition using the SVD of MATLAB (registered trademark) as the analysis tool, a component waveform diagram for each component was created in accordance with the singular value S, and the diagrams were analyzed to determine the presence/absence of correlation between the amplitude of the component waveform and each of the brain resting time and the brain activated time. In this test, the same device described above was used as the infrared thermography device. The infrared camera was set in front of the subject at a position 1.5 m away from the subject.

When acquiring the photographic image data of the facial surface using the imaging device, in some cases sunlight or the like strikes the facial surface while imaging, reflects off the facial surface, and this reflected light enters the lens of the imaging device. In such cases, this reflected light may be recorded in the captured photographic image data of the facial surface. Here, in the RBG data obtained from the photographic image data, changes in brightness based on the facial blood circulation volume are smaller than changes in brightness based on reflected light. Consequently, if blood circulation volume calculated on the basis of RGB data obtained from photographic image data with the reflected light recorded therein is analyzed, it is considered that the RGB changes in the facial surface unrelated to brain activity (i.e. noise) could be mixed into the data. Therefore, in order to prevent the mixing of such RGB changes in the facial surface that were unrelated to brain activity, relative blood circulation volume data was created from relative RGB data obtained by setting an average of all of the RGB data taken every 30 seconds at "0". Then, the thus-created blood circulation volume data was also subjected to singular value decomposition using the SVD of MATLAB (registered trademark) as the analysis tool, and the component waveform diagram and the blood circulation volume distribution diagram for each component were created in accordance with the singular value S. Then, the diagrams are analyzed to identify a component indicating an RGB change of the facial surface that reflects brain activity.

For the sake of convenience, in the following description, the relative blood circulation volume data based on relative RGB data, for which the average of all of the RGB data obtained every predetermined time period (every 30 seconds in this test) is set to "0", is referred to as "relative conversion blood circulation volume data"; whereas the blood circulation volume data based on the RGB data before converting to the relative RGB data is referred to simply as "blood circulation volume data."

Additionally, while acquiring the time-series photographic image data of the facial surfaces of the six subjects using the imaging device, electrodes were connected to the scalps of the subjects and electroencephalogram were taken. Evaluations were conducted for correlation between the amplitude of the component waveform diagrams and the amplitude of the $\beta$ wave, which are known as a waveform that appears when awake or when brain cells are active (brain waves in the 13 to 30 Hz frequency range). Note that, when taking the electroencephalograms, the electrodes were arranged at 19 sites (Fp1, Fp2, F3, F4, C3, C4, P3, P4, O1, O2, F7, F8, T3, T4, T5, T6, Fz, Cz, and Pz) on the scalp specified by the International 10-20 System.

Furthermore, it can be expected that the heads of the subjects may move vertically while the brain function activation task is given to the subjects. If such movement occurs, the positions of the faces of the subjects with respect to the imaging device will change. A control test was conducted on one subject in order to verify whether such changes in the position of the face influence the RGB changes in the facial surface. In the control test, as in the test described above, the imaging device was used to acquire the time-series photographic image data of the facial surface of the subject. However, in this case, the subject was instructed to operate the keyboard at random timings during the period in which the brain function activation task was not given (that is, during brain resting time). Furthermore, the time-series blood circulation volume data, based on the RGB data obtained from the time-series photographic image data of the facial surface captured in the control test, was subjected to singular value decomposition using the SVD of MATLAB (registered trademark) as the analysis tool, a component waveform diagram for each component was created in accordance with the singular value S. Then, the diagrams were analyzed to determine the presence/absence of correlation between the amplitude of the component waveform and each of the brain resting time and the brain activated time. Additionally, an analysis was conducted to determine the presence/absence of correlation between the amplitude of each component waveform and actual facial movement. The actual facial movement was evaluated by acquiring, from the photographic image data, a two-dimensional coordinate of a point corresponding to an actual point at the face, and calculating a movement distance of the face every 30 seconds when imaging. In these calculations, the photographic image data at the start of the control test was used as a reference. Furthermore, an analysis was also conducted to determine the presence/absence of correlation between the amplitude of each component waveform and the number of inputs on the keyboard during imaging. The number of inputs on the keyboard during imaging was evaluated by calculating a simple moving average every 30 seconds in the time-series photographic image data.

(3) Analysis Results

In the following description, "the components 1, 2 . . . " are numbered in descending order of the singularity value. Each component represents a percentage in the entire dispersion, and influences with large changes are reflected in component 1. Specifically, influences of motions of the subject and external noise tends to be reflected in component 1. As a result, the influence of brain activity is frequently reflected in the component waveform of component 2 rather than that of component 1.

(3-1) Facial Skin Temperature Data Analysis Results

Figure 2A:
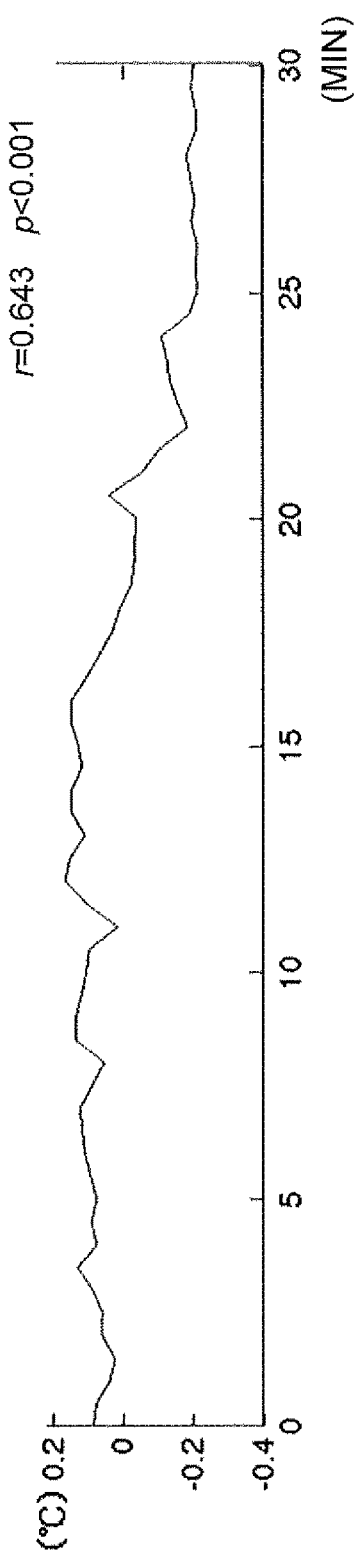
FIGS. 2A and 2B illustrate a portion of the results of analyzing facial skin temperature data.
Figure 2B:
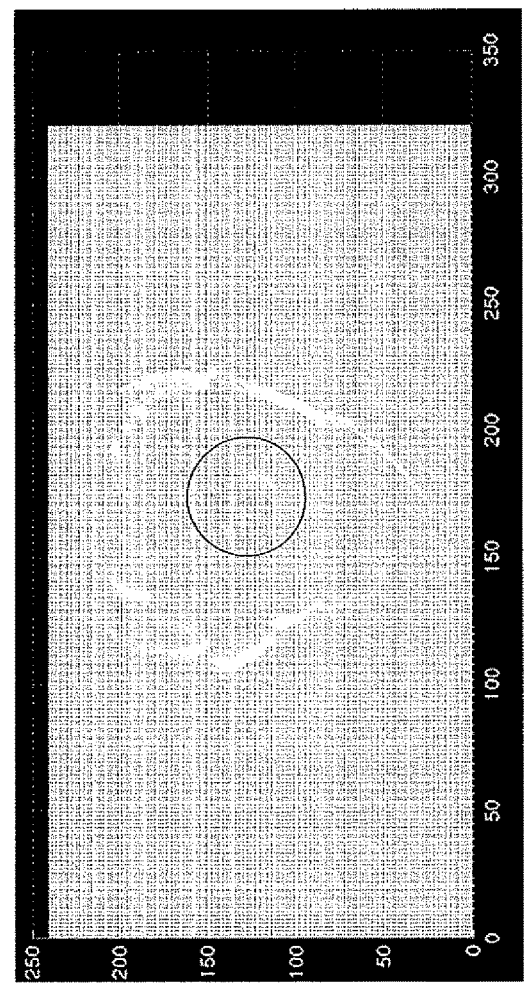
Figure 3A:
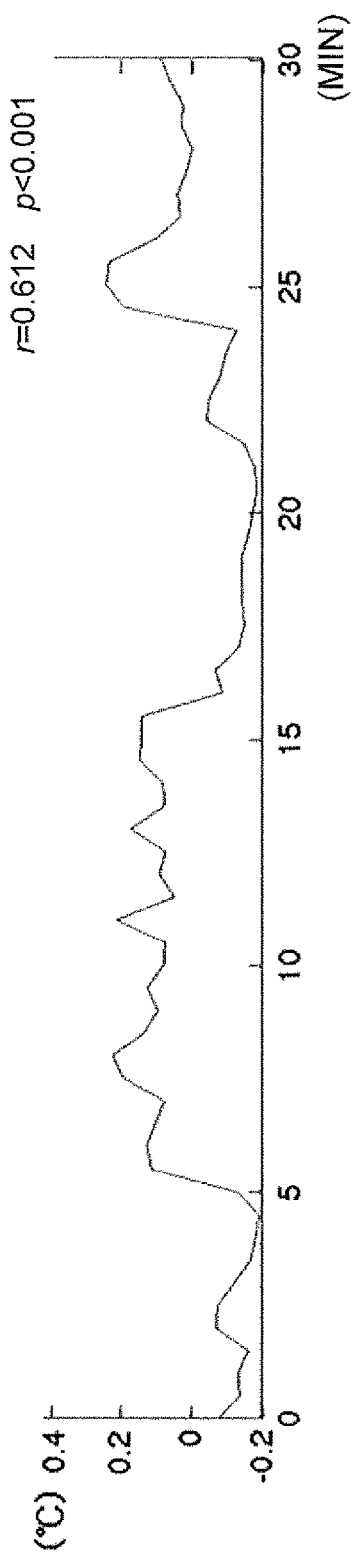
FIGS. 3A and 3B illustrate a portion of the results of analyzing the facial skin temperature data.
Figure 3B:
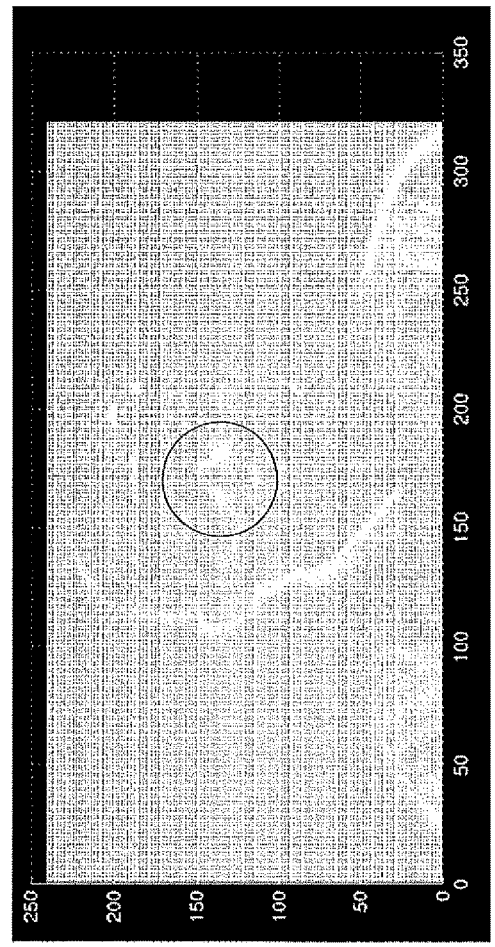
Figure 4:
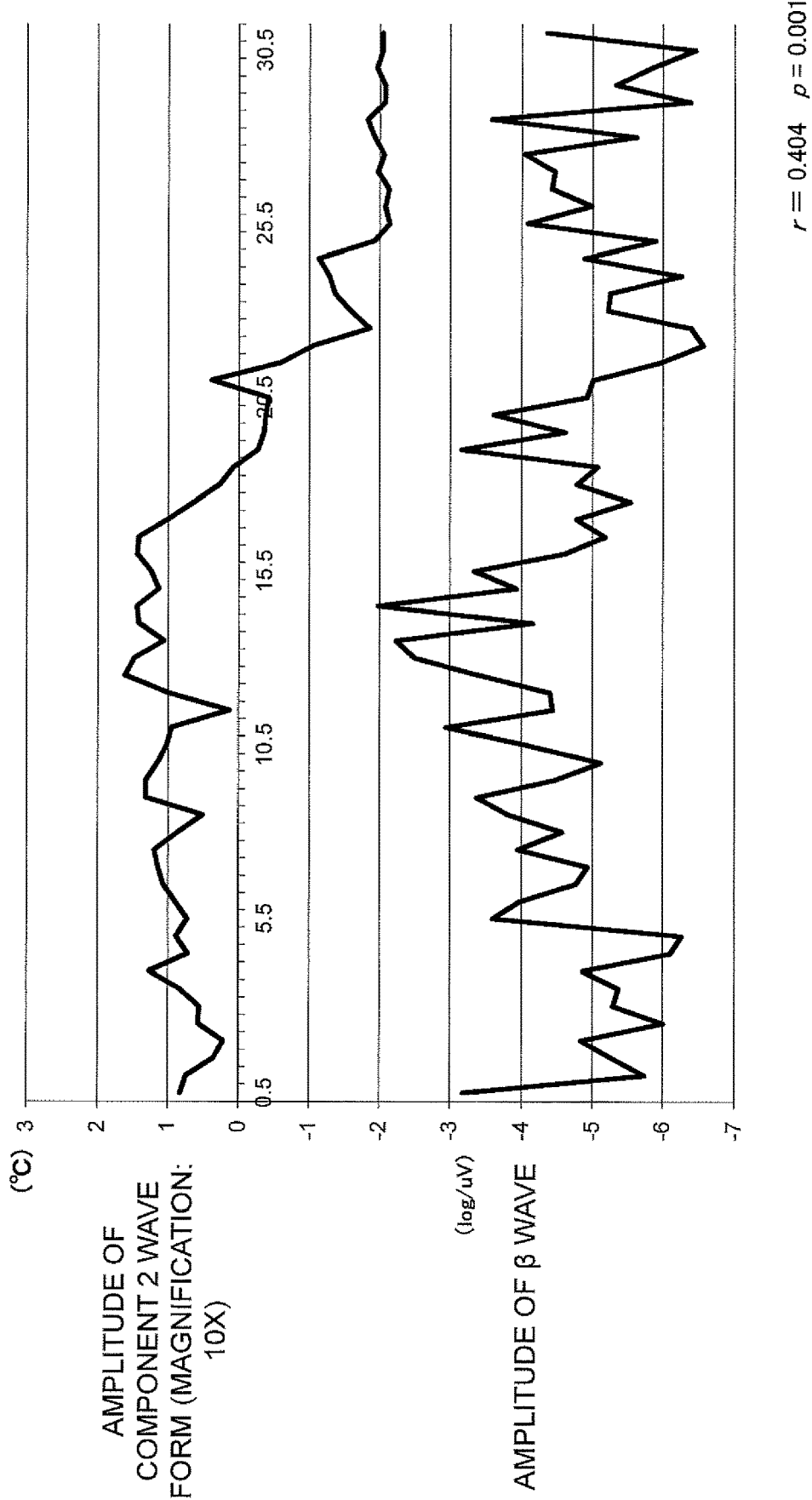
FIG. 4 is a chart illustrating the amplitude of a component waveform of a component 2, and the amplitude of the $\beta$ wave of the measured brain waves.
Figure 5:
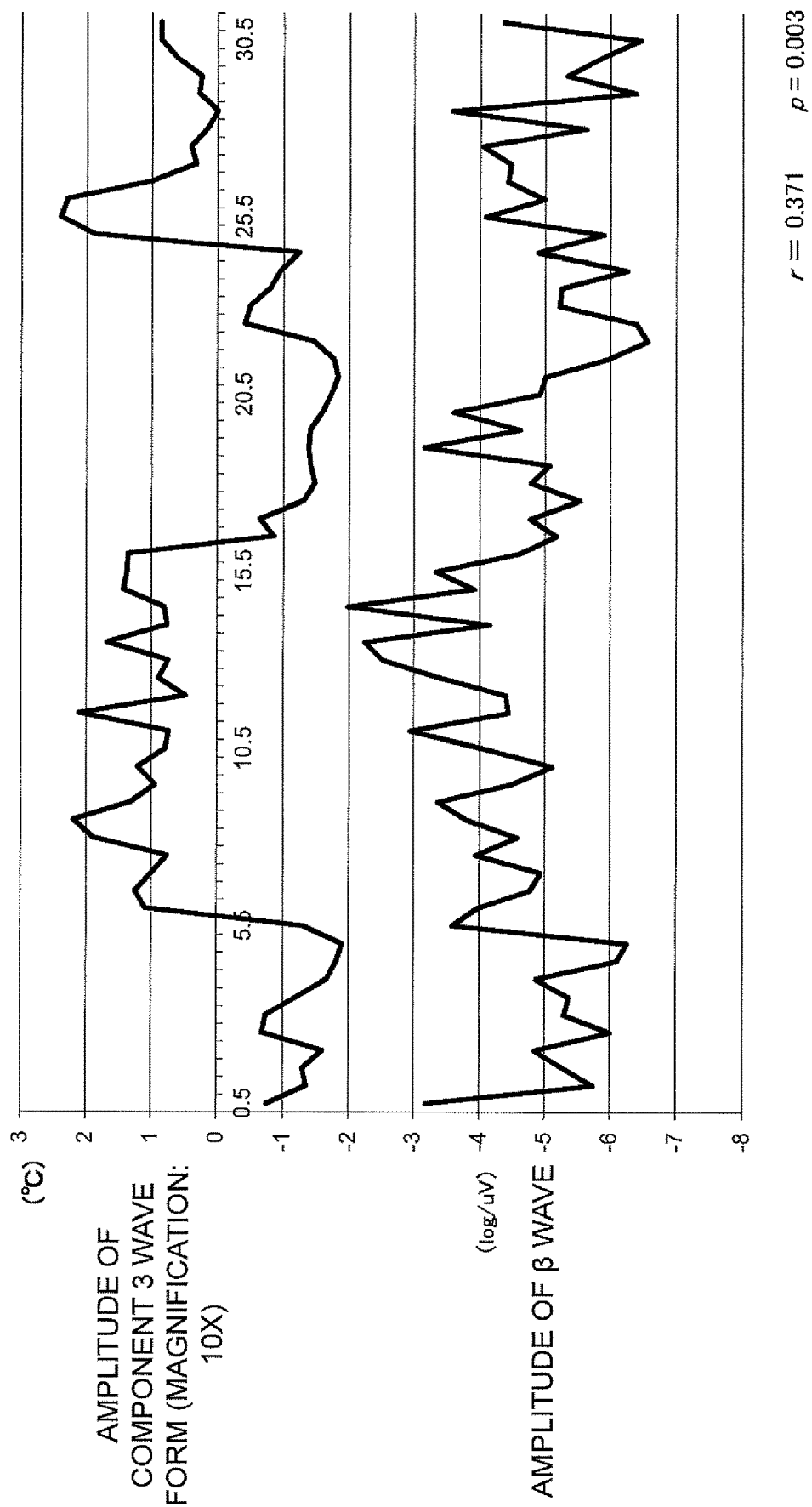
FIG. 5 is a chart illustrating the amplitude of a component waveform of a component 3, and the amplitude of the $\beta$ wave of the measured brain waves.
Figure 6A:
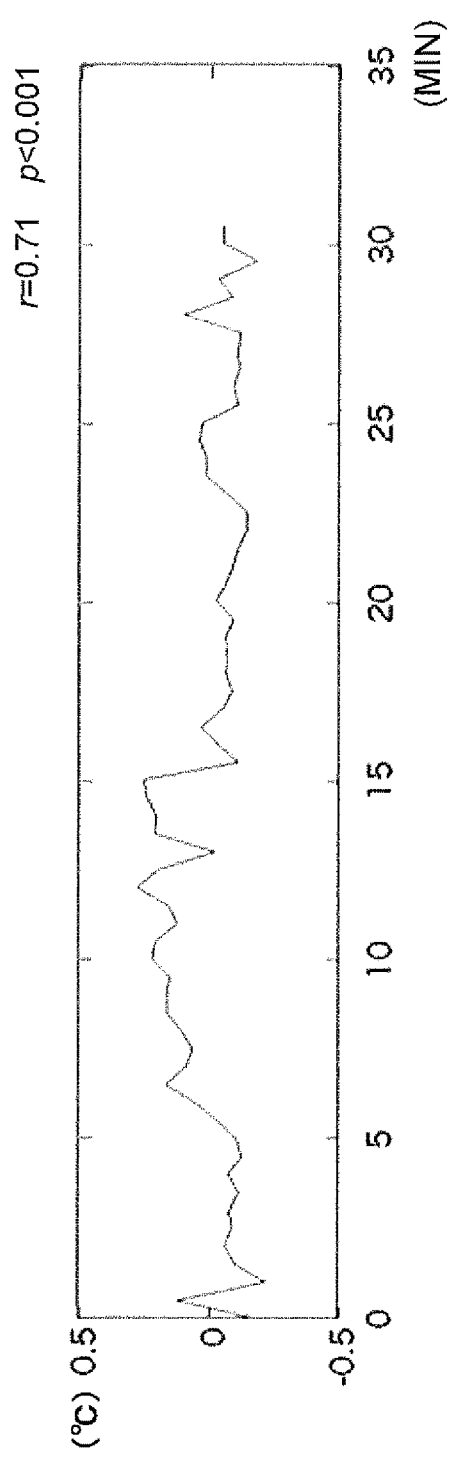
FIGS. 6A and 6B are a chart illustrating a portion of the results of analyzing the facial skin temperature data obtained in a control test.
Figure 6B:
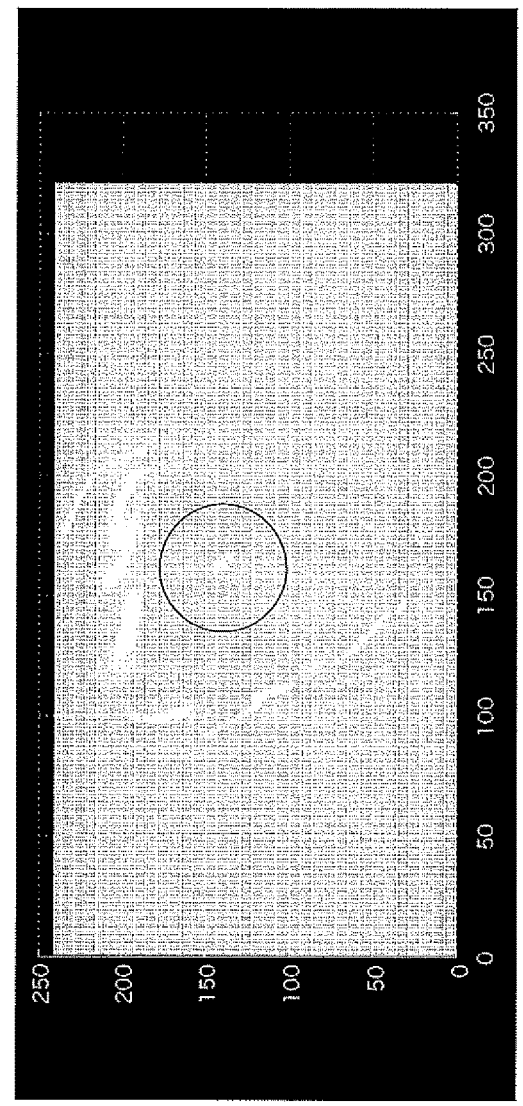

FIG. 2 illustrates a portion of the results of analyzing the facial skin temperature data based on the temperature conversion data. FIG. 2A illustrates the component waveform diagram of a component 2 of a subject 1. FIG. 2B illustrates the temperature distribution diagram of the component 2 of the subject 1. FIG. 3A illustrates the component waveform diagram of a component 3 of the subject 1. FIG. 3B illustrates the temperature distribution diagram of the component 3 of the subject 1. FIGS. 4 and 5 illustrate relationships between the amplitudes of the component waveforms and brain waves. FIG. 4 illustrates the amplitude of the component waveform of the component 2 of the subject 1, and the amplitude of the β wave of the measured brain waves. FIG. 5 illustrates the amplitude of the component waveform of the component 3 of the subject 1, and the amplitude of the β wave of the measured brain waves. FIGS. 6A and 6B illustrate a portion of the results of analyzing the facial skin temperature data obtained in the control test. FIG. 6A illustrates the component waveform diagram of the component 3. FIG. 6B illustrates the temperature distribution diagram of the component 3.

Table 1 shows the results of analyzing the facial skin temperature data for each subject.

From the results obtained by analyzing the facial skin temperature data described above, significant correlation was found between human brain activity and the component 2 and/or the component 3 of the plurality of components obtained by decomposing the time-series facial skin temperature data by singular value decomposition.

TABLE 1

| Subject | Correlation in Data Based on Absolute Temperature Conversion Data | | Correlation in Data Based on Relative Temperature Conversion Data | |
| --- | --- | --- | --- | --- |
| | Component waveform | Temperature distribution | Component waveform | Temperature distribution |
| Subject 1 | Component 2, Component 3 | Component 2, Component 3 | Component 2, Component 3 | Component 2, Component 3 |
| Subject 2 | Component 3 | Component 3 | Component 3 | Component 3 |
| Subject 3 | Component 1, Component 2, Component 3 | Component 2, Component 3 | Component 2, Component 3 | Component 2, Component 3 |
| Subject 4 | Component 2, Component 3 | Component 2, Component 3 | Component 2, Component 3 | Component 2, Component 3 |
| Subject 5 | Component 2, Component 3 | Component 2, Component 3 | Component 2, Component 3 | Component 2, Component 3 |
| Subject 6 | Component 2, Component 5 | Component 2, Component 5 | Component 2, Component 5 | Component 2, Component 5 |

As illustrated in FIGS. 4 and 5, from the results of analyzing the brain waves, significant correlation was found between the amplitude of the β wave of the brain waves and the amplitudes of the component 2 and the component 3.

Furthermore, in the control test, even in states where the subject moved while the brain function activation task was not being given, there was significant correlation between the component 3 and human brain activity (see FIG. 6). From these results, it was found that movement by the subject when acquiring the facial skin temperature data does not influence the component 3 of the plurality of components.

Based on these results, the present inventors made the following findings.

The time-series facial skin temperature data acquired from the subjects were decomposed into the plurality of components by singular value decomposition. As a result of analyzing each of the decomposed components, it was found that the component 3 of the plurality of components is a component that is related to brain activity. Specifically, it was found that it is possible to identify a component indicating a change in skin temperature that reflects brain activity from the plurality of components by decomposing the time-series facial skin temperature data into the plurality of components by singular value decomposition, extracting components having correlation with the activation/resting of the brain from the decomposed plurality of components, and analyzing the extracted components using the selective brain cooling system. Thus, the present inventors found that it is possible to estimate brain activity on the basis of human facial skin temperature.

(3-2) Results of Analyzing Photographic Image Data of Facial Surface

Figure 7:
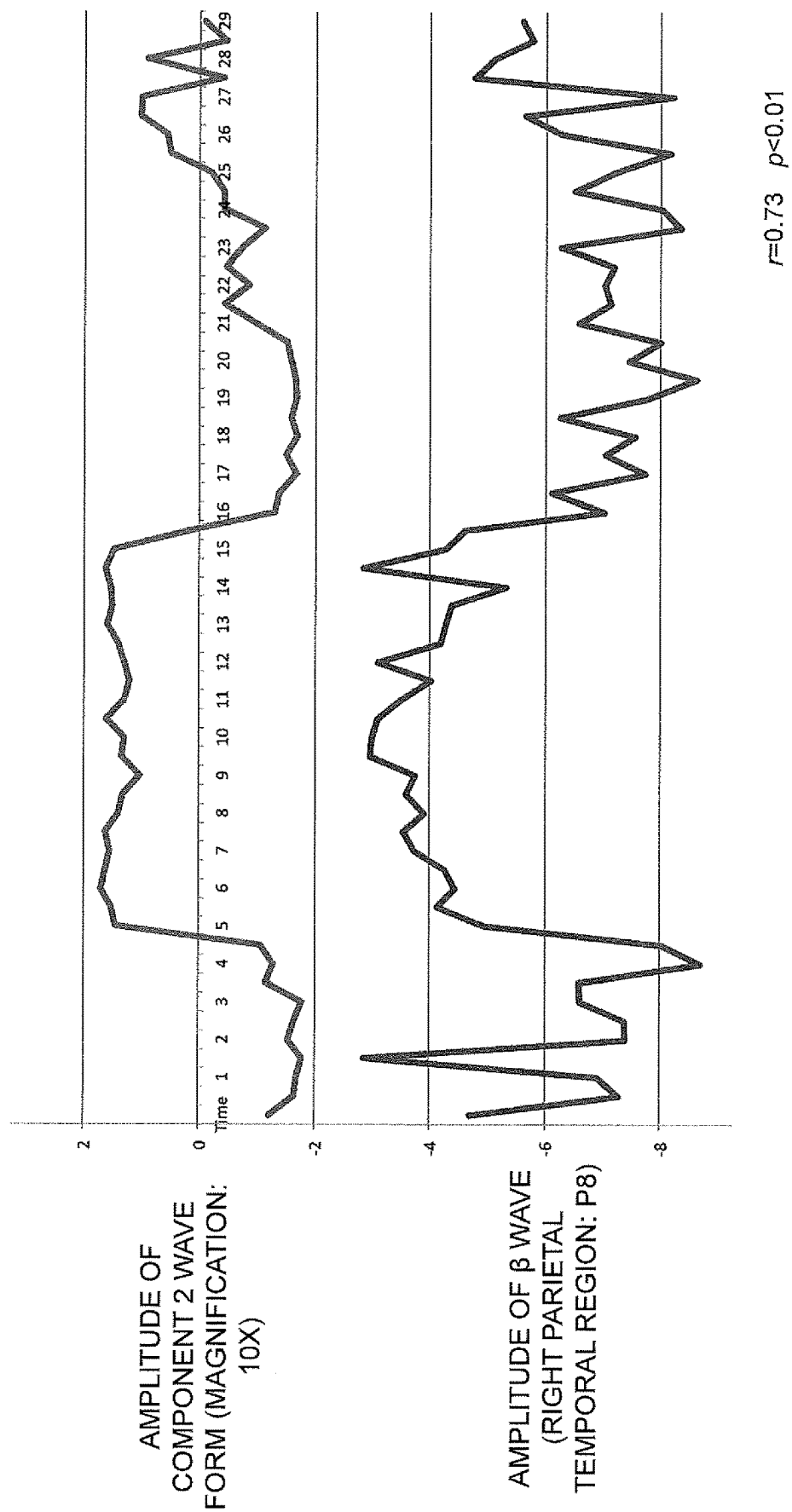
FIG. 7 is a chart illustrating a component waveform based on photographic image data of the facial surface, and the amplitude of the $\beta$ wave of the measured brain waves.
Figure 8:
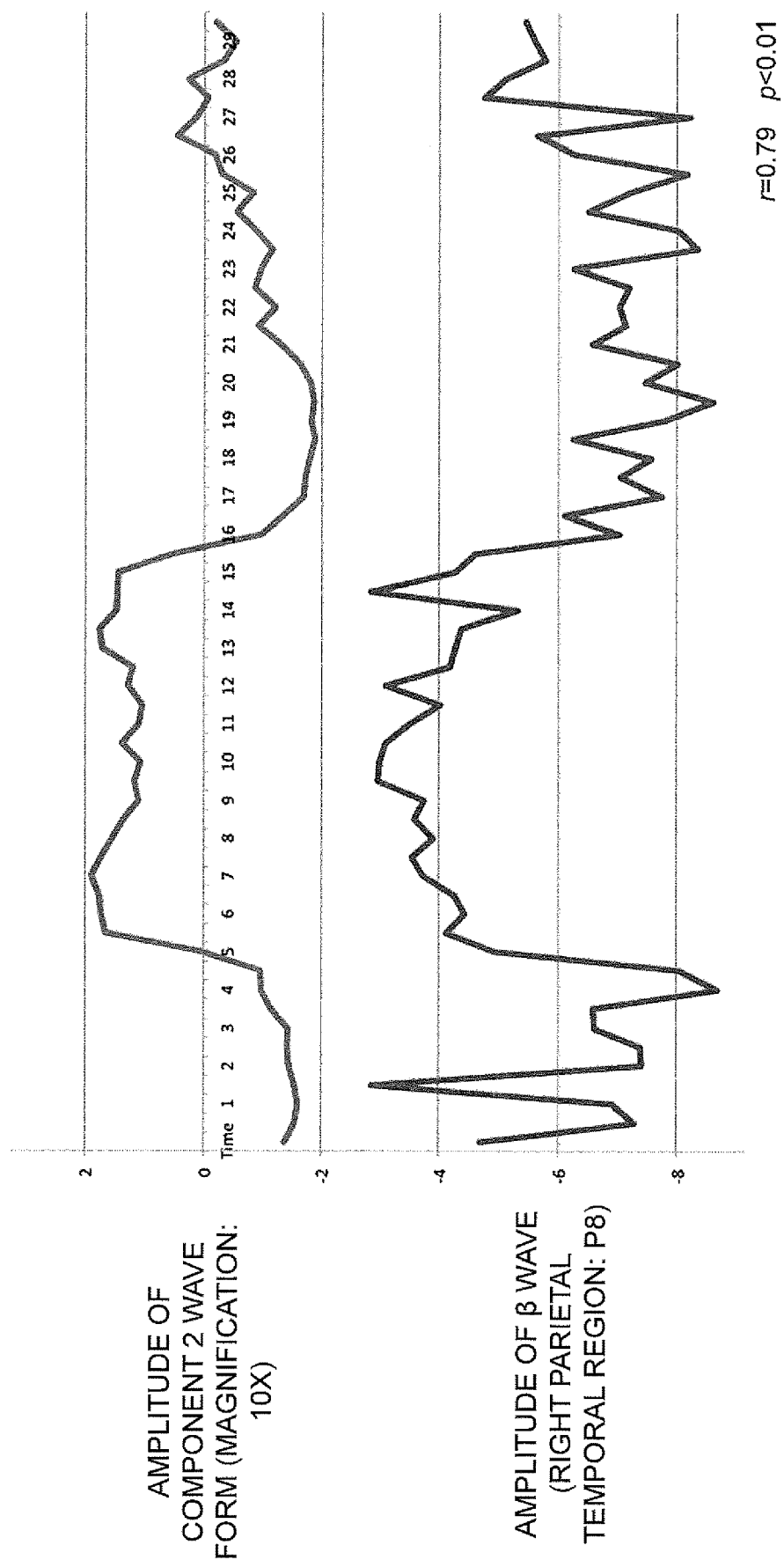
FIG. 8 is a chart illustrating a component waveform based on facial skin temperature data and the amplitude of the $\beta$ wave of the measured brain waves.
Figure 9:
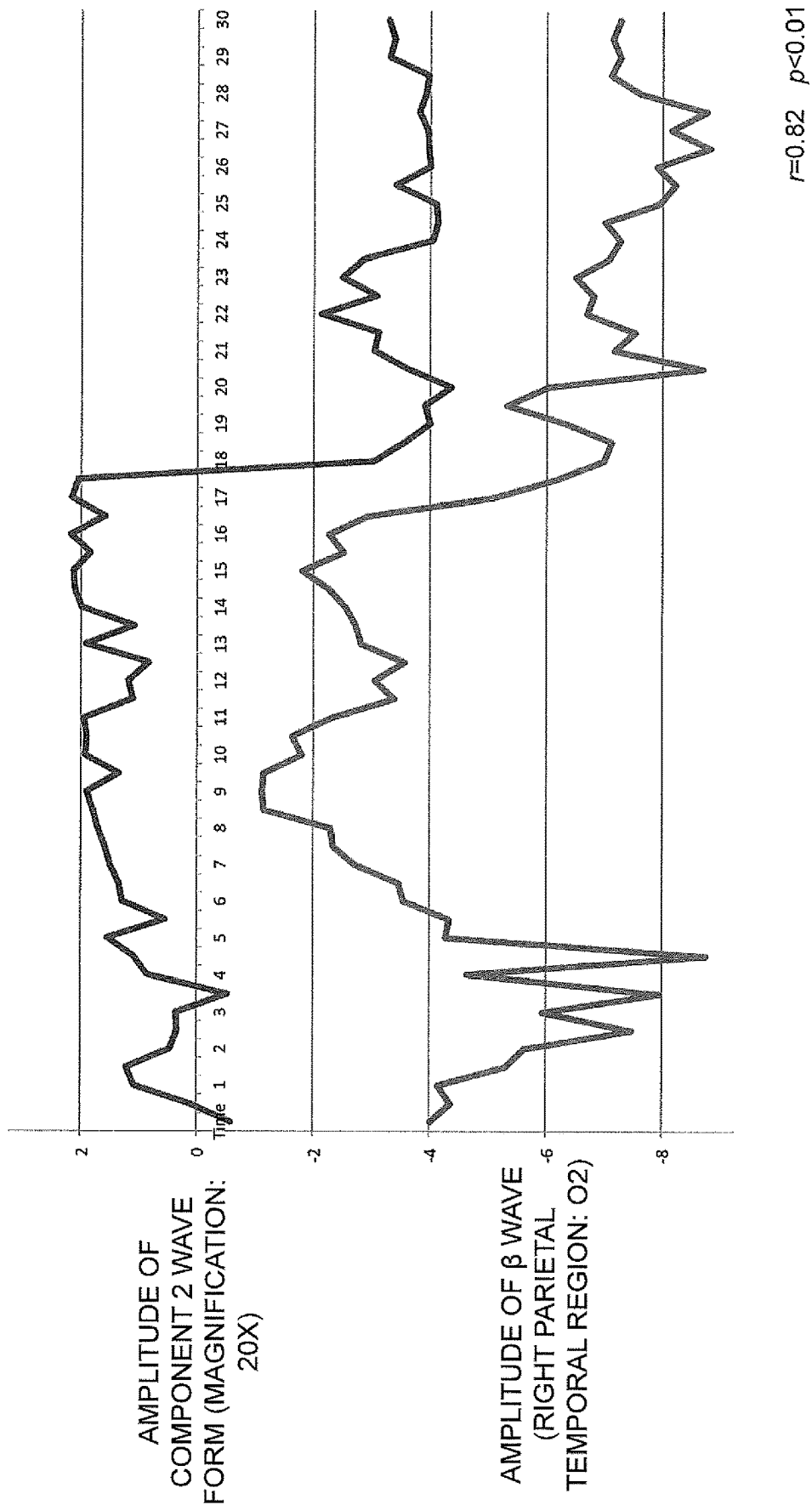
FIG. 9 is a chart illustrating a component waveform based on photographic image data of the facial surface, and the amplitude of the $\beta$ wave of the measured brain waves.
Figure 10:
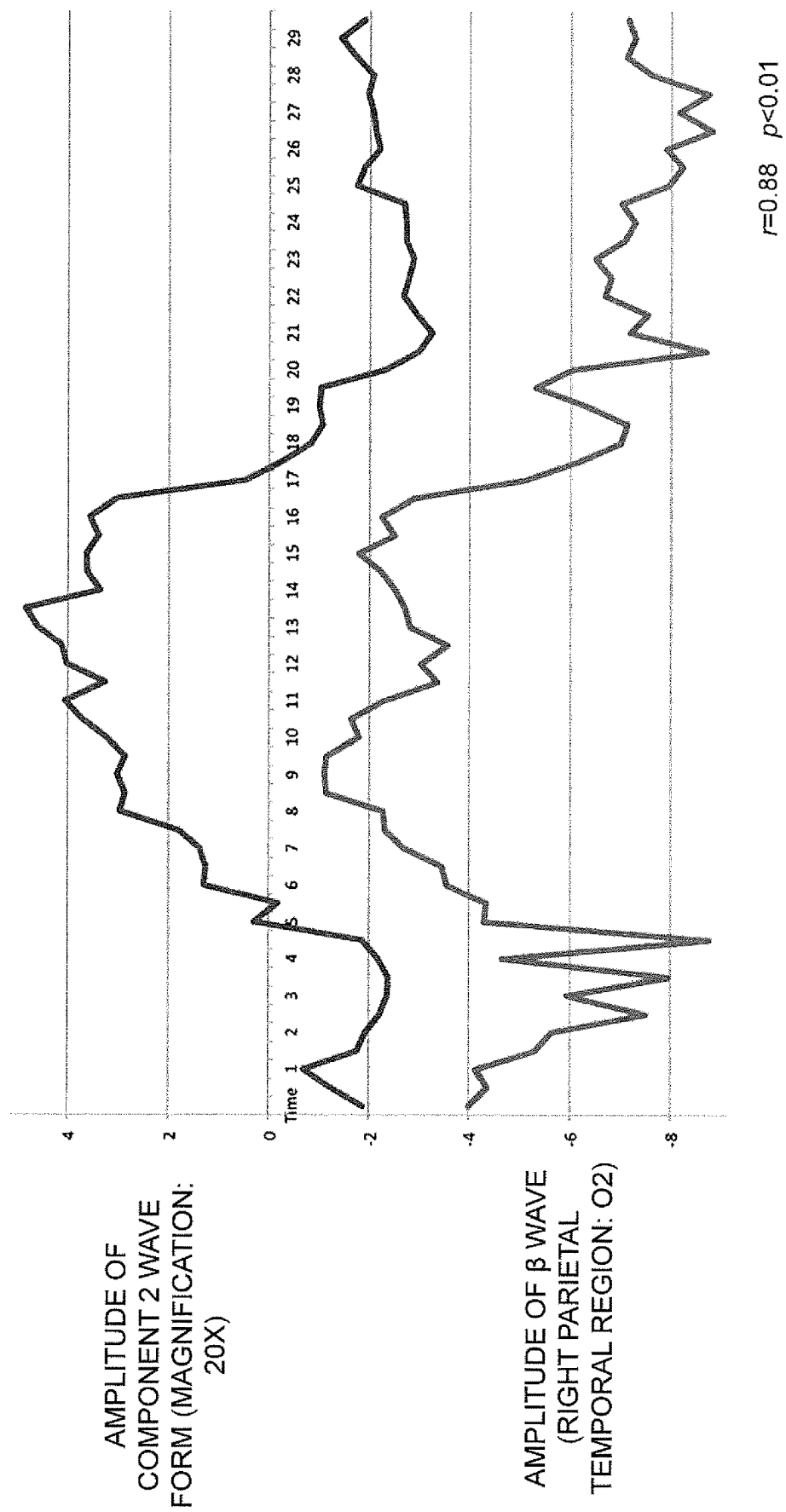
FIG. 10 is a chart illustrating a component waveform based on facial skin temperature data, and the amplitude of the $\beta$ wave of the measured brain waves.
Figure 11:
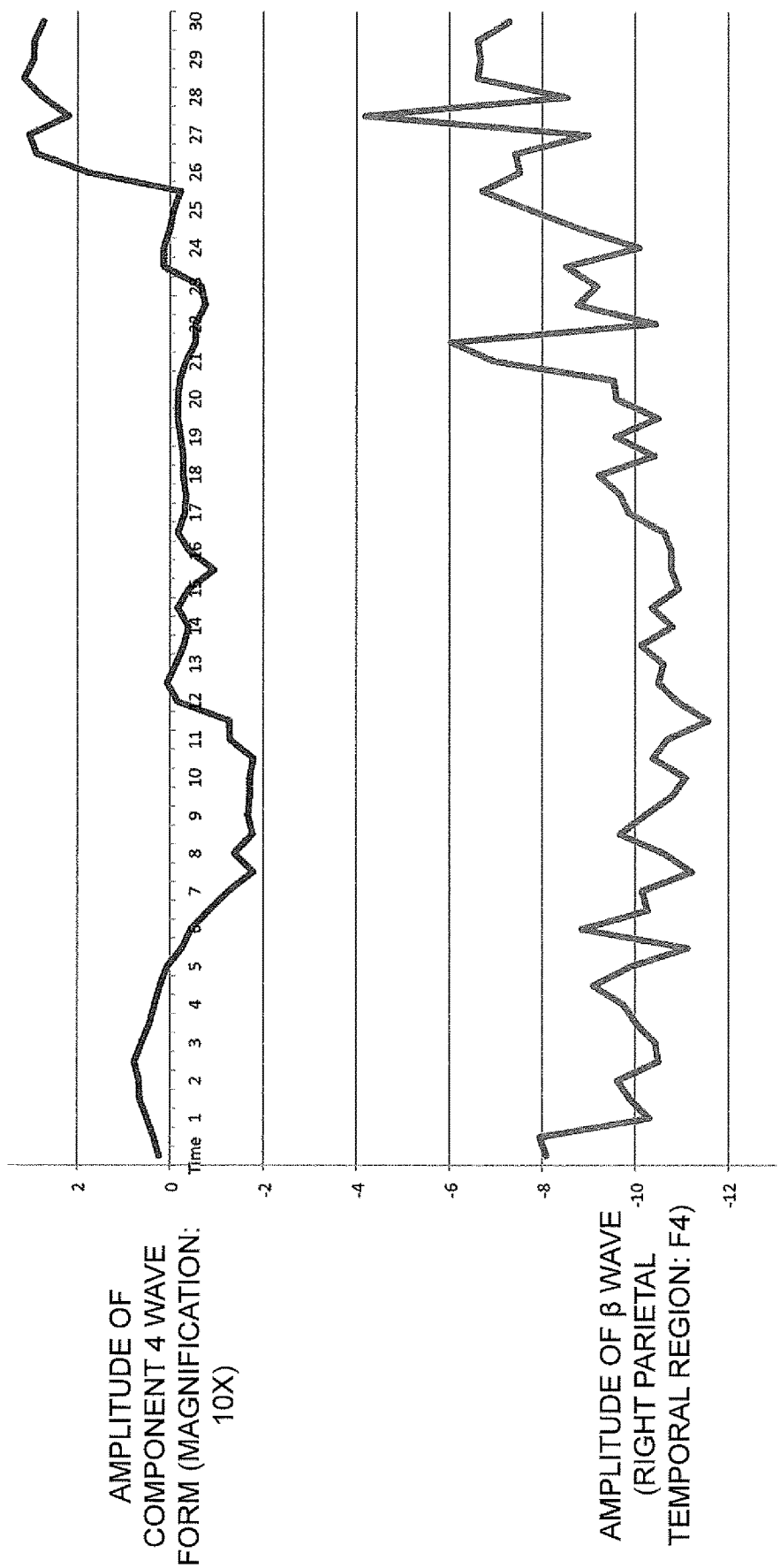
FIG. 11 is a chart illustrating a component waveform based on photographic image data of the facial surface, and the amplitude of the $\beta$ wave of the measured brain waves.
Figure 12:
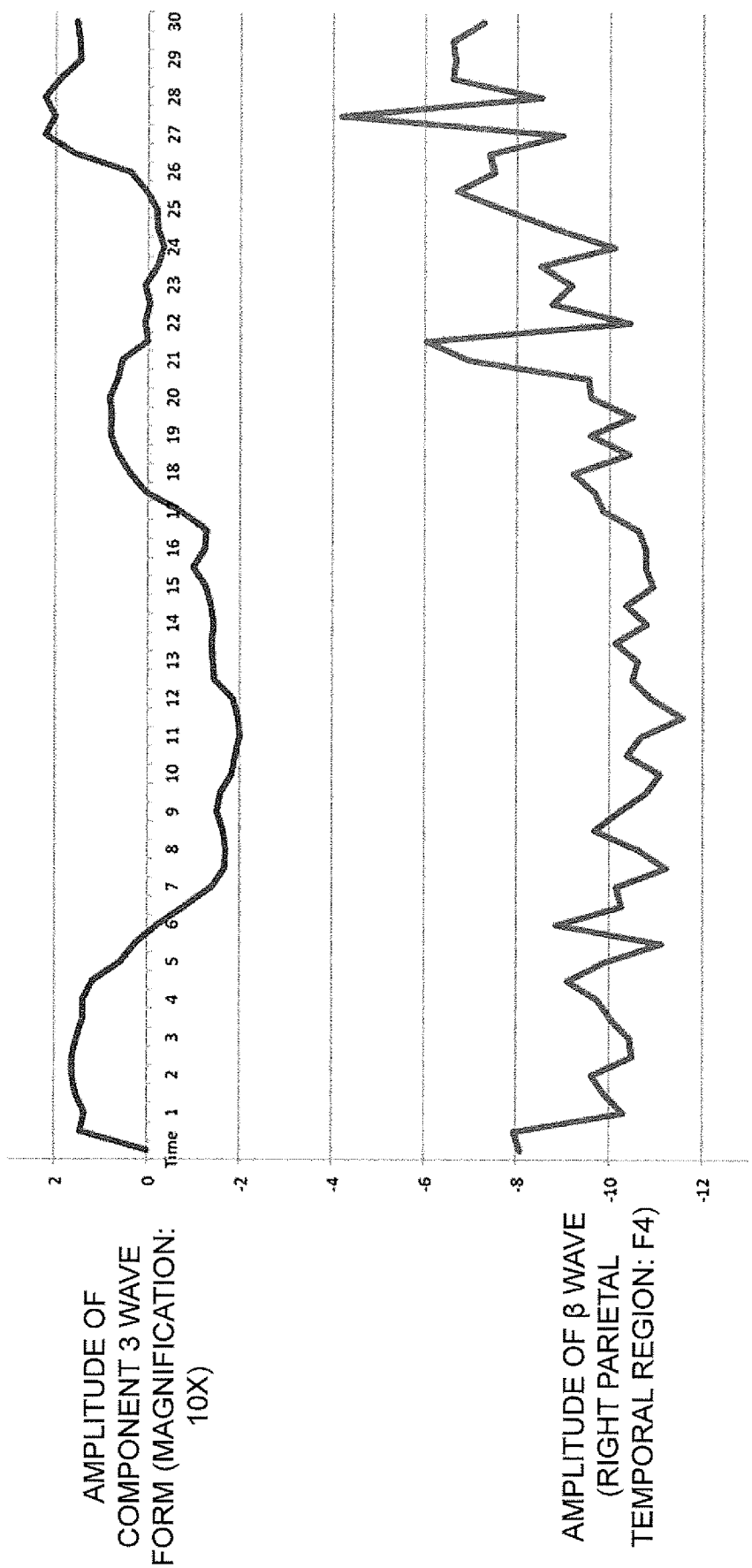
FIG. 12 is a chart illustrating a component waveform based on facial skin temperature data, and the amplitude of the $\beta$ wave of the measured brain waves.
Figure 13:
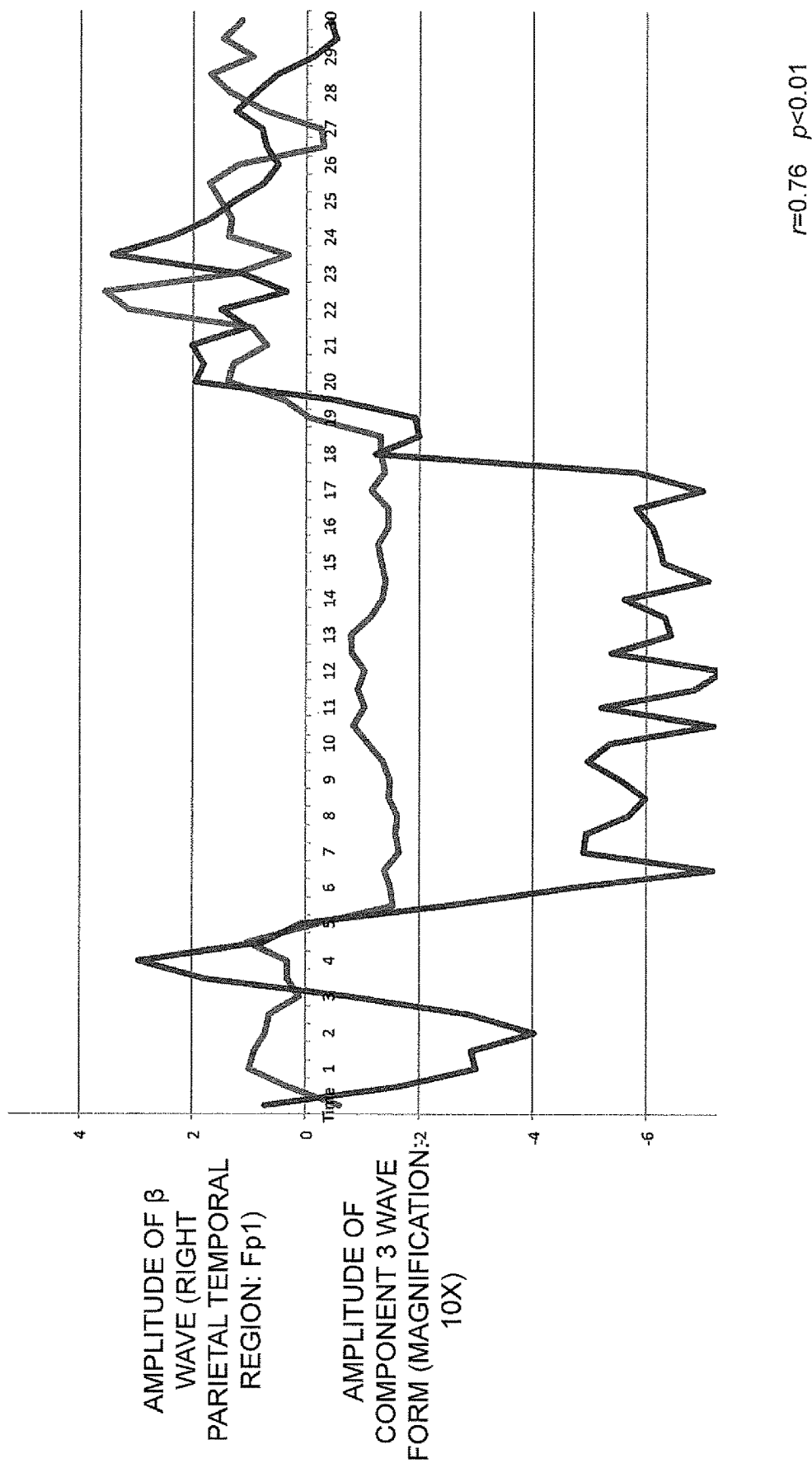
FIG. 13 is a chart illustrating a component waveform based on photographic image data of the facial surface, and the amplitude of the $\beta$ wave of the measured brain waves.
Figure 14:
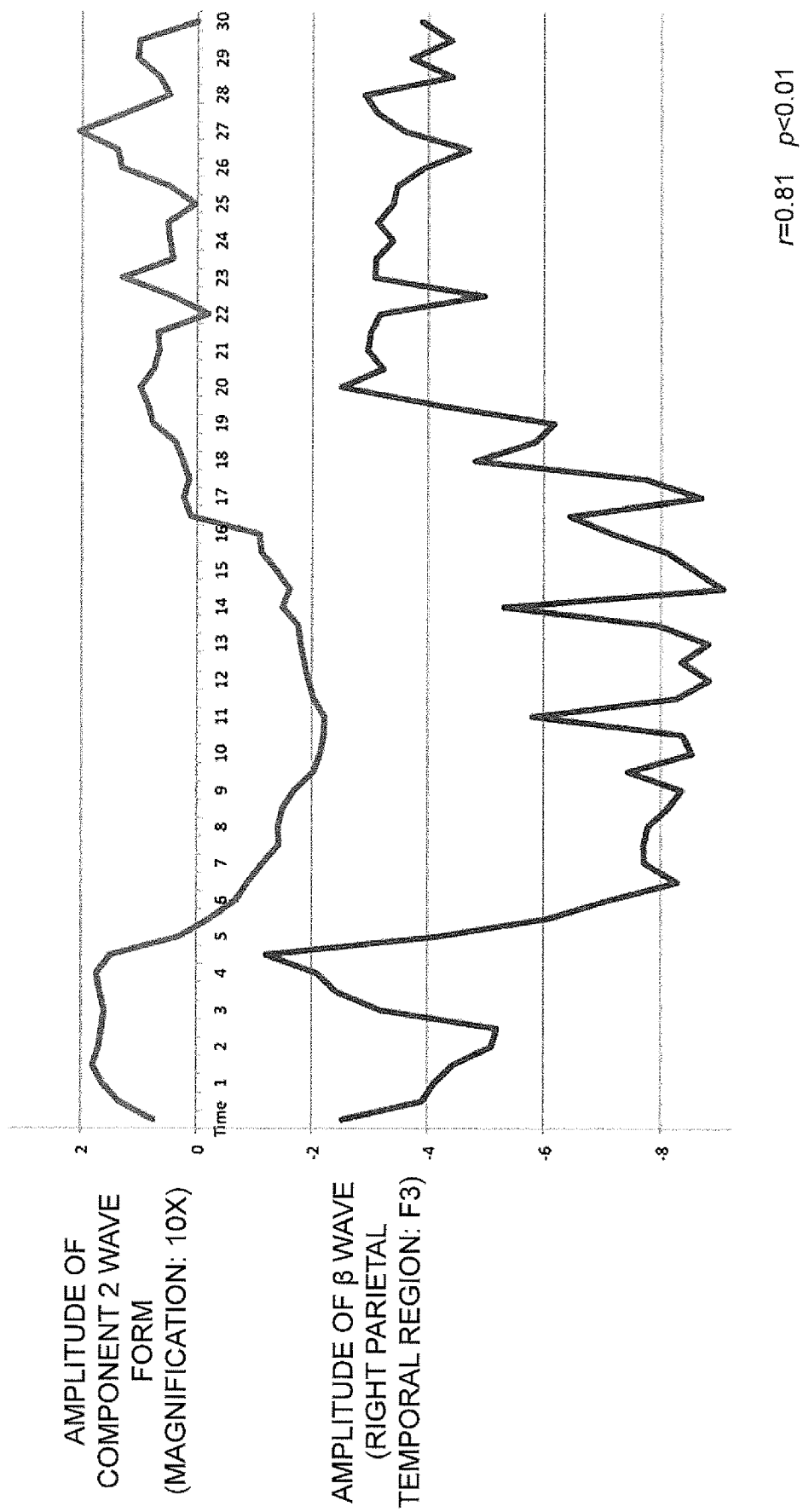
FIG. 14 is a chart illustrating a component waveform based on facial skin temperature data, and the amplitude of the $\beta$ wave of the measured brain waves.
Figure 15:
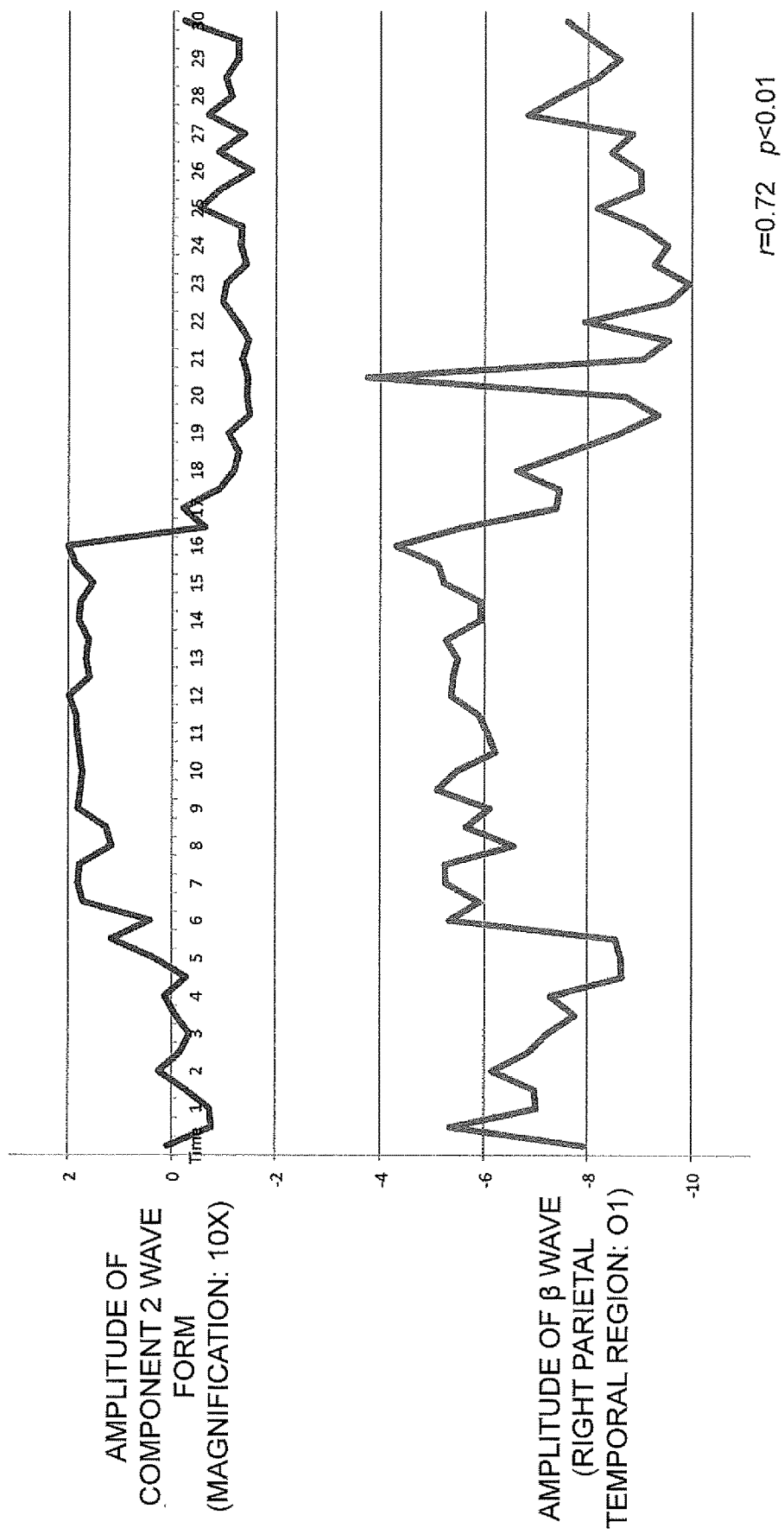
FIG. 15 is a chart illustrating a component waveform based on photographic image data of the facial surface, and the amplitude of the $\beta$ wave of the measured brain waves.
Figure 16:
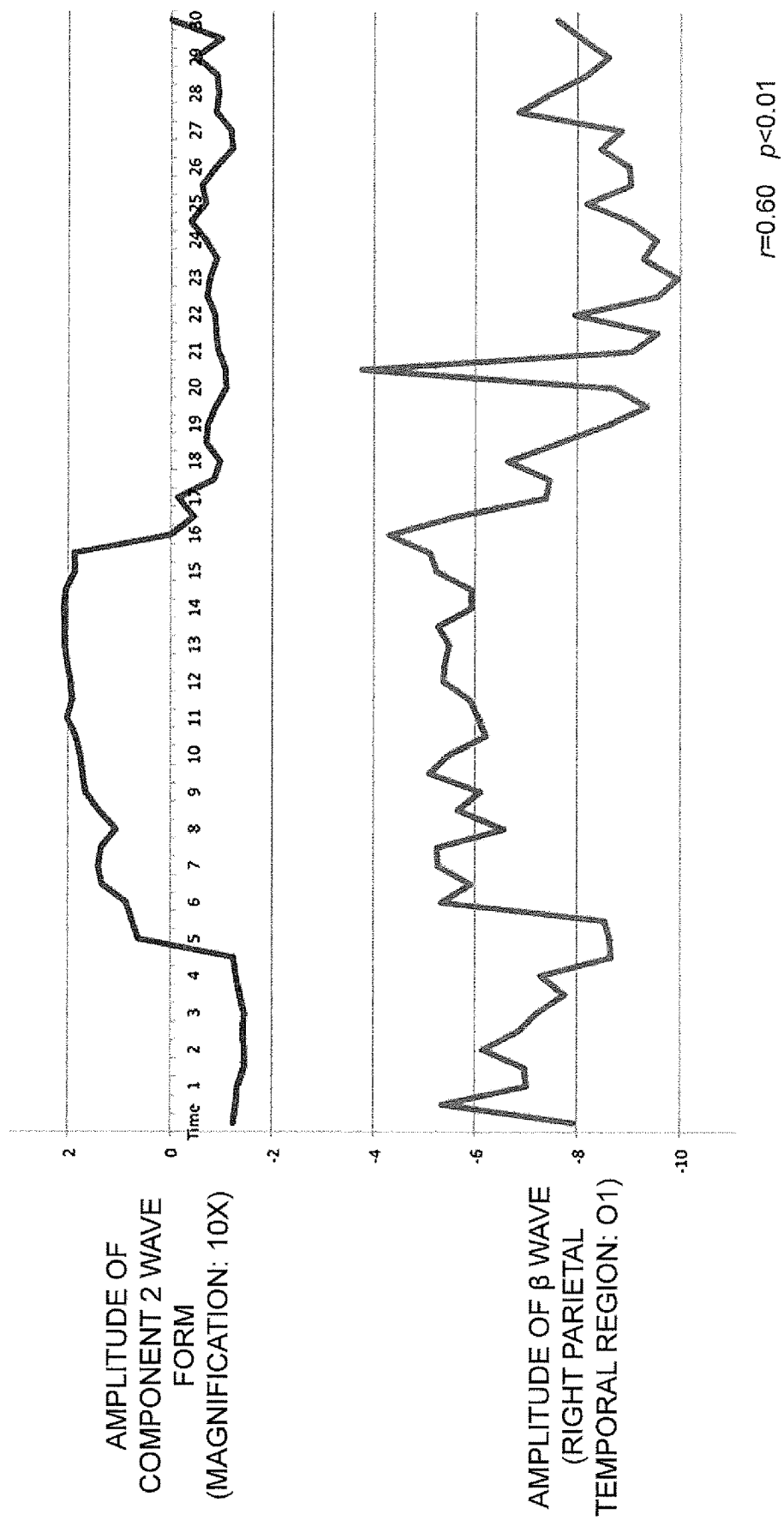
FIG. 16 is a chart illustrating a component waveform based on facial skin temperature data, and the amplitude of the $\beta$ wave of the measured brain waves.
Figure 17:
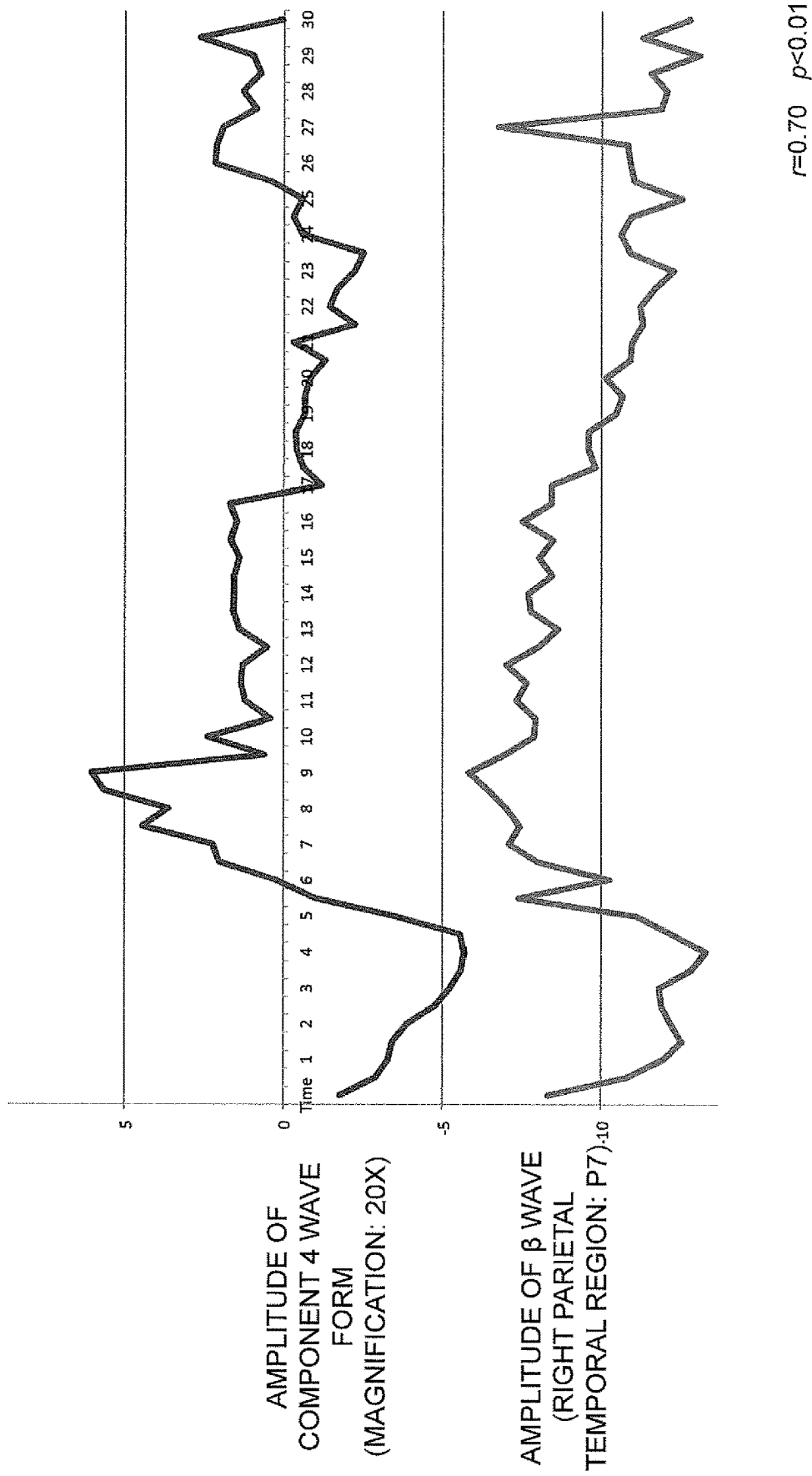
FIG. 17 is a chart illustrating a component waveform based on photographic image data of the facial surface, and the amplitude of the $\beta$ wave of the measured brain waves.
Figure 18:
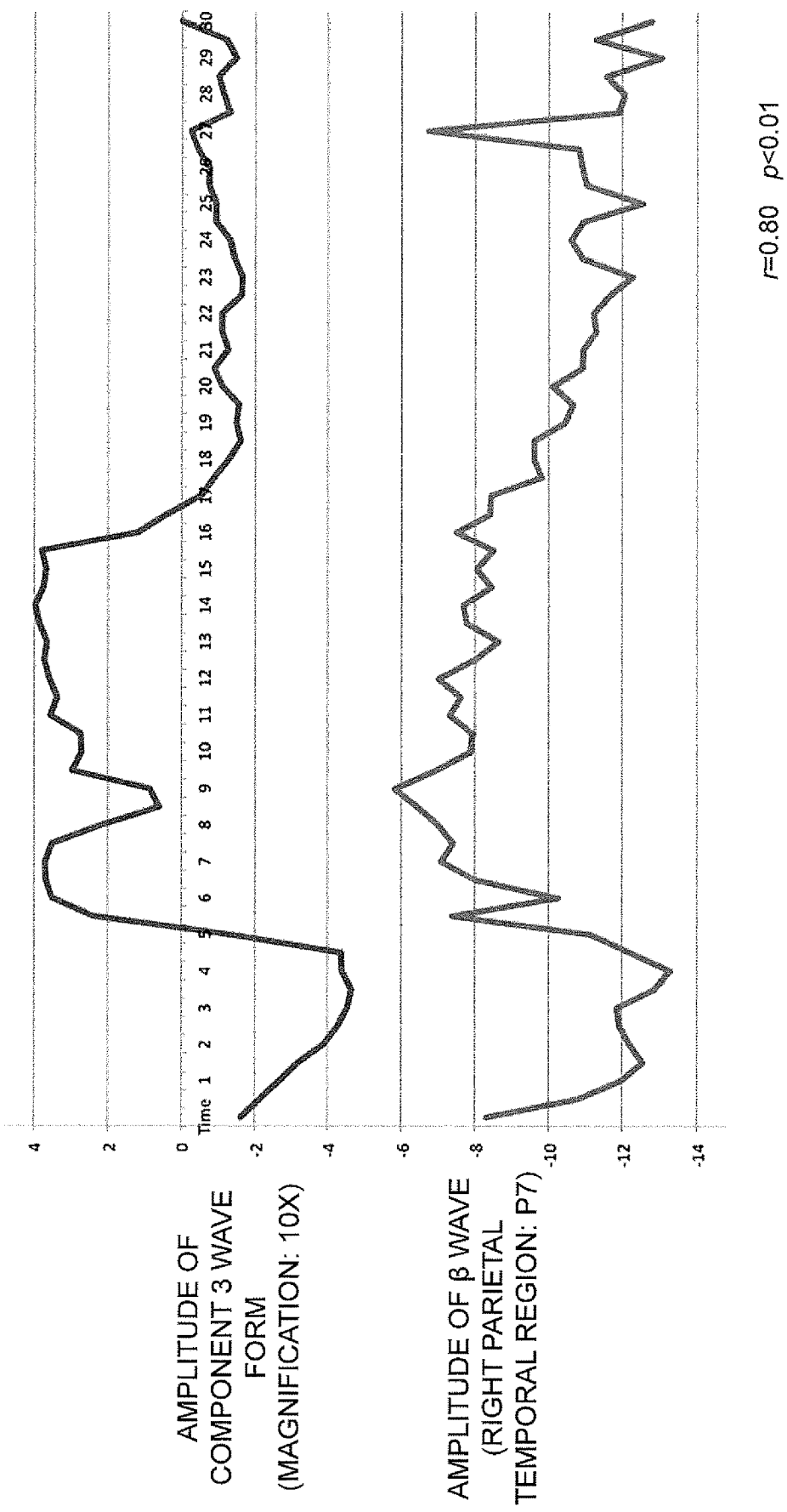
FIG. 18 is a chart illustrating a component waveform based on facial skin temperature data, and the amplitude of the $\beta$ wave of the measured brain waves.

FIGS. 7 to 18 illustrate portions of the results of comparing-analyzing component waveforms based on the photographic image data of the facial surface (blood circulation volume data) or facial skin temperature data, and the waveform diagrams of the β wave of the measured brain waves. FIG. 7 illustrates the amplitude of the component waveform of the component 2 based on the photographic image data of the subject 1, and the amplitude of the β wave of the measured brain waves of the subject 1. FIG. 8 illustrates the amplitude of the component waveform of the component 2 based on the facial skin temperature data of the subject 1, and the amplitude of the β wave of the measured brain waves of the subject 1. FIG. 9 illustrates the amplitude of the component waveform of the component 2 based on the photographic image data of a subject 2, and the amplitude of the β wave of the measured brain waves of the subject 2. FIG. 10 illustrates the amplitude of the component waveform of the component 2 based on the facial skin temperature data of the subject 2, and the amplitude of the β wave of the measured brain waves of the subject 2. FIG. 11 illustrates the amplitude of the component waveform of a component 4 based on the photographic image data of a subject 3, and the amplitude of the β wave of the measure d brain waves of the subject 3. FIG. 12 illustrates the amplitude of the component waveform of the component 3 based on the facial skin temperature data of the subject 3, and the amplitude of the β wave of the measured brain waves of the subject 3. FIG. 13 illustrates the amplitude of the component waveform of the component 3 based on the photographic image data of a subject 4, and the amplitude of the β wave of the measured brain waves of the subject 4. FIG. 14 illustrates the amplitude of the component waveform of the component 2 based on the facial skin temperature data of the subject 4, and the amplitude of the β wave of the measured brain waves of the subject 4. FIG. 15 illustrates the amplitude of the component waveform of the component 2 based on the photographic image data of the subject 5, and the amplitude of the β wave of the measured brain waves of the subject 5. FIG. 16 illustrates the amplitude of the component waveform of the component 2 based on the facial skin temperature data of the subject 5, and the amplitude of the β wave of the measured brain waves of the subject 5. FIG. 17 illustrates the amplitude of the component waveform of a component 4 based on the photographic image data of a subject 6, and the amplitude of the β wave of the measured brain waves of the subject 6. FIG. 18 illustrates the amplitude of the component waveform of the component 2 based on the facial skin temperature data of the subject 2, and the amplitude of the β wave of the measured brain waves of the subject 2.

As illustrated in FIGS. 7 to 18, from the results of the component waveforms and brain wave analyses, correlation was found between the facial skin temperature and the facial blood circulation volume. In each of the analyses based on the facial skin temperature data and the facial blood circulation volume data, significant correlation was found between the amplitude of each component waveform and the amplitude of the β wave measured by the electrodes attached to the top or back of the head.

Table 2 shows the results of analyzing the photographic image data of the facial surface of each subject.

TABLE 2

| Subject | Correlation in Blood Circulation Volume Data | | Correlation in Relative Conversion Blood Circulation Volume Data | |
| --- | --- | --- | --- | --- |
| | Component waveform | Blood circulation volume distribution | Component waveform | Blood circulation volume distribution |
| Subject 1 | Component 2 | 0.72 | Component 1 | 0.59 |
| | | | Component 2 | 0.85 |
| Subject 2 | Component 1 | 0.82 | Component 1 | 0.62 |
| | Component 2 | 0.82 | Component 2 | 0.60 |
| Subject 3 | Component 2 | 0.33 | Component 2 | 0.45 |
| | | | Component 3 | 0.56 |
| | Component 3 | 0.31 | Component 4 | 0.56 |
| Subject 4 | Component 1 | 0.57 | Component 1 | 0.66 |
| | Component 3 | 0.71 | Component 3 | 0.65 |
| Subject 5 | Component 1 | 0.56 | Component 1 | 0.51 |
| | Component 2 | 0.72 | Component 2 | 0.83 |
| Subject 6 | Component 2 | 0.38 | Component 2 | 0.45 |
| | | | Component 3 | 0.51 |
| | Component 4 | 0.68 | Component 5 | 0.36 |

As shown in Table 2, from the results obtained by analyzing the photographic image data of the facial surface described above, significant correlation was found between human brain activity and the components 1, 2, 3, 4, and 5 of the plurality of components obtained by decomposing the time-series blood circulation volume data based on the photographic image data of the facial surface by singular value decomposition. Note that, in this case, the components found to have significant correlation based on the blood circulation volume data and significant correlation based on the relative conversion blood circulation volume data were determined to have the significant correlation with human brain activity and, in addition, the components that did not have significant correlation based on the blood circulation volume data but did have significant correlation based on the relative conversion blood circulation volume data were also determined to have the significant correlation with human brain activity.

Table 3 shows the results of the control test.

TABLE 3

| | |
|---|---|
| Components having correlation with brain resting time/brain activated time | Component 1, Component 2 |
| Components having correlation with movement distance of face | Component 1, Component 3, Component 4 |
| Components having correlation with number of keyboard inputs | Component 8 |

As shown in Table 3, in the control test, in cases where the subject moved while the brain function activation task was not being given, there was significant correlation between the amplitudes of component waveforms for the components 1 and 2 and each of the brain resting time and brain activated time. For component 2, in cases where the subject moved while the brain function activation task was not being given, there was not significant correlation with the movement distance and the number of keyboard inputs, respectively. As such, it was confirmed that, among the plurality of components that were obtained by conducting the singular value decomposition to the blood circulation volume data based on the RGB data acquired from the photographic image data of the facial surface, a component having significant correlation with brain activity could be influenced by the movement of the subject while acquiring the time-series photographic image data of the facial surface, but this influence was much smaller than the influence resulting from the brain activity (the influence resulting from the activation or resting of the brain).

Based on these results, the present inventors made the following findings.

The blood circulation volume data, obtained from the RGB data of the facial surface based on time-series photographic image data of the facial surface acquired from the subjects, was decomposed into the plurality of components by singular value decomposition. As a result of analyzing each of the decomposed components, it was found that the components 1, 2, 3, 4, and 5 of the plurality of components are components that are related to brain activity. Specifically, it was found that it is possible to identify, from the plurality of components, a component indicating an RGB change in the facial surface that reflects brain activity by decomposing the blood circulation volume data, obtained from the RGB data of the facial surface based on the time-series photographic image data of the facial surface into the plurality of components, by singular value decomposition, extracting components having correlation with the activation/resting of the brain from the decomposed plurality of components, and analyzing the extracted components. Thus, the present inventors found that it is possible to estimate brain activity on the basis of time-series photographic image data of a human facial surface.

(4) Brain Activity Visualization Device

Next, brain activity visualization devices 10, 110 according to an embodiment of the present invention will be described. The brain activity visualization devices 10, 110 were conceived by the inventor on the basis of the findings described above. The brain activity visualization devices according to the present invention should not be construed as being limited to the following embodiments, and various types of modifications may be made without departing from the spirit or scope of the general inventive concept of the present invention.

The brain activity visualization devices 10, 110 according to the embodiment of the present invention include brain activity estimation means 30 that estimate brain activity on the basis of facial skin temperature data, and/or brain activity estimation means 130 that estimate brain activity on the basis of photographic image data of the facial surface. Before describing the brain activity visualization devices 10, 110 according to the embodiment of the present invention, each of the brain activity estimation means 30, 130 will be described.

Figure 19:
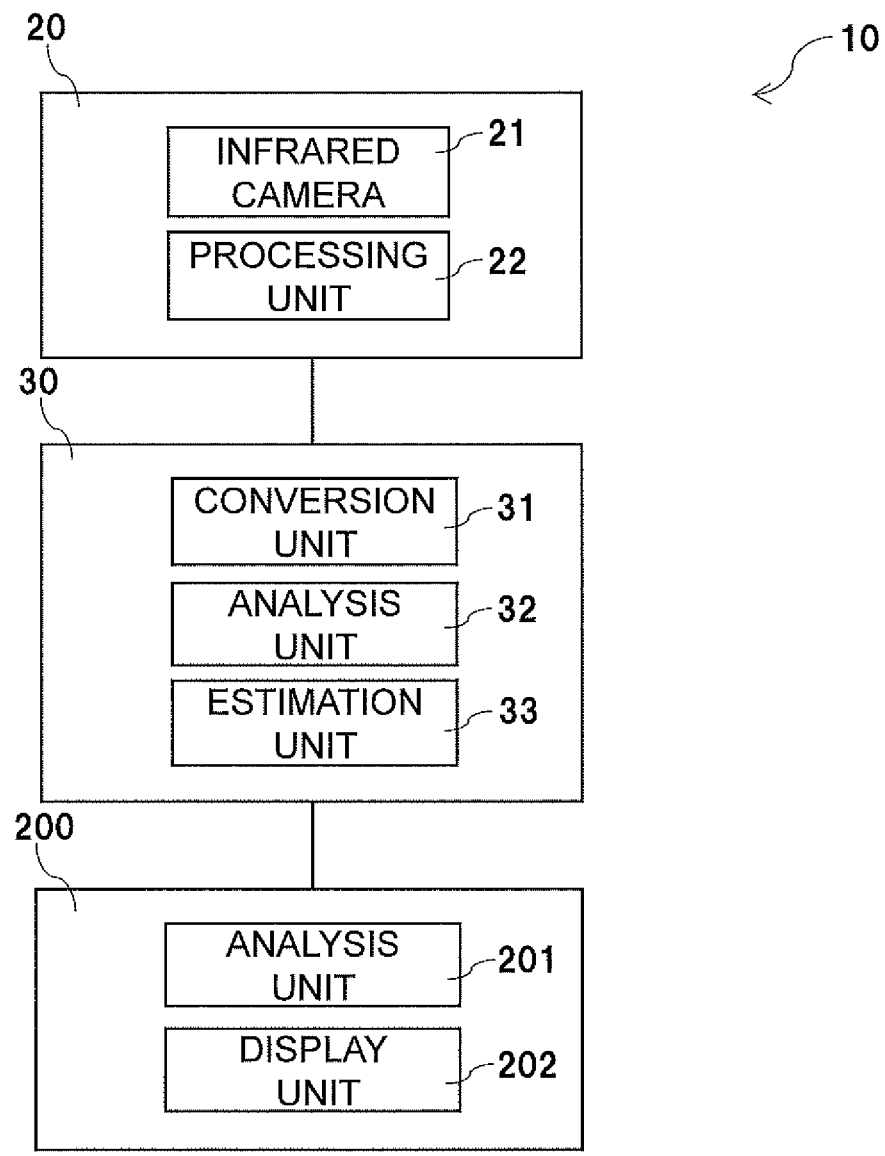
FIG. 19 is a schematic drawing of a brain activity visualization device according to an embodiment of the present invention.
Figure 20:
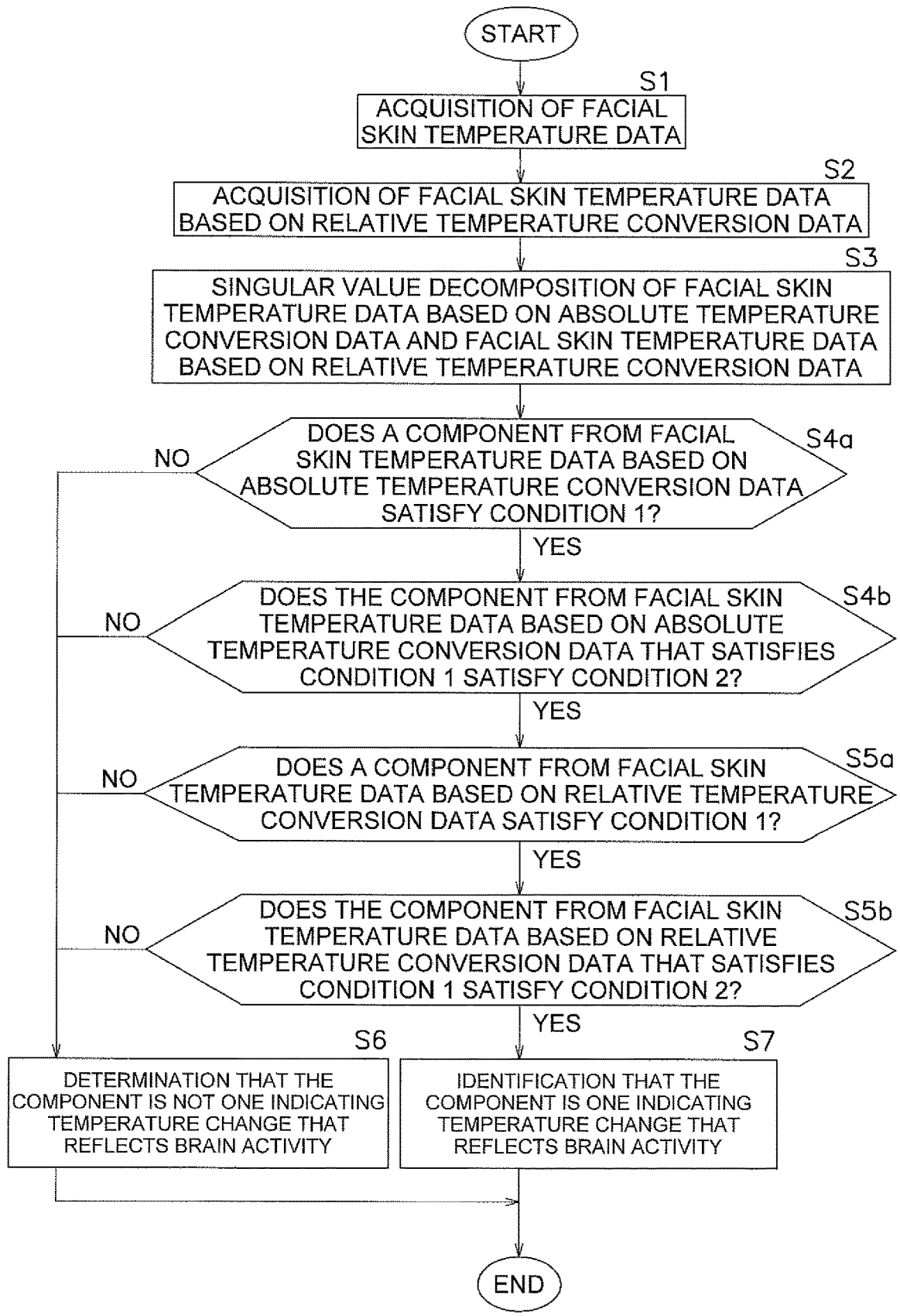
FIG. 20 is a flowchart showing an example of the flow of processing conducted in the brain activity visualization device to identify a component indicating a change in skin temperature that reflects brain function.

(4-1) Brain Activity Estimation Means 30 that Estimate Brain Activity on the Basis of Facial Skin Temperature Data FIG. 19 is a schematic drawing of the brain activity visualization device 10 according to the embodiment of the present invention. FIG. 20 is a flowchart showing the flow of processing conducted in the brain activity visualization device 10 to identify a component indicating a change in skin temperature that reflects brain function.

The brain activity estimation means 30 of the brain activity visualization device 10 estimate the brain activity of an individual (subject) from the facial skin temperature of the individual. As illustrated in FIG. 19, the brain activity visualization device 10 includes facial skin temperature acquisition means 20, the brain activity estimation means 30, and state visualization means 200.

The facial skin temperature acquisition means 20 detect the skin temperature of at least a portion of the facial surface of the individual, and chronologically acquire facial skin temperature data including detected temperature data and position data of the detection site (step S1). Note that, in this case, the facial skin temperature acquisition means 20 is an infrared thermography device and includes an infrared camera 21 and a processing unit 22 as illustrated in FIG. 19. The infrared camera 21 is configured to detect infrared radiant energy emitted from the facial surface of the individual. Moreover, in this case, the infrared camera 21 is configured to detect infrared radiant energy emitted from the entire facial surface of the individual. The processing unit 22 converts the infrared radiant energy detected by the infrared camera 21 to temperatures to create temperature data. The processing unit 22 generates a temperature distribution diagram of the facial skin temperature of the entire facial surface, for which the sites where the infrared radiant energy was detected are used as the position data (coordinate data). The processing unit 22 processes the generated temperature distribution diagram as facial skin temperature data based on temperature conversion data. The processing unit 22 has a storage unit (not illustrated in the drawings) and the facial skin temperature data based on temperature conversion data is stored in this storage unit.

An example is described in which the temperature distribution diagram of the facial skin temperature of the whole facial surface is generated in the processing unit 22, but the present invention is not limited thereto. For example, a configuration is possible in which a temperature distribution diagram of facial skin temperature including at least the forehead and/or the area around the paranasal sinuses is generated and used as the facial skin temperature data based on temperature conversion data.

Additionally, in this case, a brain function activation task is given to the individual for a set period of time while the facial skin temperature acquisition means 20 are acquiring the facial skin temperature data based on temperature conversion data. That is, the facial skin temperature data based on temperature conversion data, acquired by the facial skin temperature acquisition means 20, contains data for a period in which the brain function activation task was being given to the individual. Note that the brain function activation task given to the individual is not particularly limited provided that the task is presumed to place the brain in an activated state, and the content thereof may be appropriately determined in accordance with the purpose of use of the brain activity visualization device 10.

The brain activity estimation means 30 estimate human brain activity on the basis of facial skin temperature data based on the temperature conversion data acquired by the facial skin temperature acquisition means 20. Specifically, the brain activity estimation means 30 include a conversion unit 31, an analysis unit 32, and an estimation unit 33 as illustrated in FIG. 19.

The conversion unit 31 converts the temperature data included in the facial skin temperature data based on temperature conversion data to relative temperature data, and generates facial skin temperature data based on the converted relative temperature data, that is, facial skin temperature data based on relative temperature conversion data (step S2). Specifically, the conversion unit 31 uses, as a reference, an average of the temperature data included in the facial skin temperature data based on temperature conversion data for every predetermined time period (e.g. 30 seconds), and converts the temperature data to relative temperature data. Then, the conversion unit 31 uses the converted relative temperature data and the position data to generate the facial skin temperature data based on relative temperature conversion data.

The analysis unit 32 decomposes each of the time-series facial skin temperature data based on temperature conversion data and the facial skin temperature data based on relative temperature conversion data into a plurality of components by singular value decomposition, principal component analysis, or independent component analysis (step S3). Here, the analysis unit 32 subjects each of the acquired facial skin temperature data based on temperature conversion data and the facial skin temperature data based on relative temperature conversion data to singular value decomposition in which the SVD of MATLAB (registered trademark) is used as the analysis tool. In the singular value decomposition, for each of the chronologically acquired facial skin temperature data based on temperature conversion data and the facial skin temperature data based on relative temperature conversion data, the factor is set to time data per predetermined time period (e.g. 30 seconds), and the measure is set to the facial skin temperature data based on temperature conversion data and the facial skin temperature data based on relative temperature conversion data in each time period. Then, the facial skin temperature data based on temperature conversion data and the facial skin temperature data based on relative temperature conversion data are each decomposed into a plurality of components by singular value decomposition. Thereafter, the analysis unit 32 calculates a time distribution, a space distribution, and a singular value representing the magnitude of each component.

Additionally, the analysis unit 32 determines whether or not each component satisfies a first condition and a second condition in order to identify a component, from the plurality of components decomposed by singular value decomposition, indicating a change in skin temperature that reflects brain activity (step S4a, step S4b, step S5a, and step S5b). Note that, in this case, the analysis unit 32 first determines whether or not each component from the facial skin temperature data based on temperature conversion data satisfies the first condition (step S4a). Then, for components from the facial skin temperature data based on temperature conversion data determined to satisfy the first condition in step S4a, the analysis unit 32 determines whether or not those components satisfy the second condition (step S4b). Then, the analysis unit 32 determines whether or not each component from the facial skin temperature data based on relative temperature conversion data, matching the components determined to satisfy the first condition and the second condition in step S4a and step S4b, satisfies the first condition (step S5a). Then, the analysis unit 32 determines whether or not the components from the facial skin temperature data based on relative temperature conversion data, which is determined to satisfy the first condition in step S5a satisfy the second condition (step S5b). However, the order of determination in the analysis unit 32 is not limited thereto and, for example a configuration is possible in which it is determined whether or not the components from the facial skin temperature data based on temperature conversion data and the components from the facial skin temperature data based on relative temperature conversion data satisfy the first condition and the second condition, and the components for which the determination results match are ultimately extracted.

The first condition is that the amplitude of the component waveform of the component decomposed by singular value decomposition has correlation with changes at brain resting time and brain activated time. The analysis unit 32 extracts, from the plurality of components, components satisfying the first condition as determination components. Note that, the brain function activation task is given to the individual for a set period of time while the facial skin temperature data based on temperature conversion data is being acquired. The brain resting time is defined as the period in which the brain function activation task is not being given to the individual, and the brain activated time is defined as the period in which the brain function activation task is being given to the individual. Here, the analysis unit 32 conducts a comparative analysis of the component waveform of each component against the periods in which the brain function activation task is and is not being given. Using the results of this comparative analysis based on the component waveform data, the analysis unit 32 evaluates whether or not there is correlation between the component waveform of each component and each of the brain resting time and the brain activated time. Then, the analysis unit 32 extracts, from the plurality of components, components evaluated as having correlation as a determination component that satisfies the first condition. Meanwhile, the analysis unit 32 determines that, among the plurality of components, a component evaluated as not having correlation is the component that does not satisfy the first condition and is not the component indicating a temperature change that reflects human brain activity (step S6).

In this case, the brain function activation task is given to the individual for a set period of time while acquiring the facial skin temperature data based on temperature conversion data, and the analysis unit 32 extracts the determination components based thereon. However, the content of the first condition, that is, the means of extracting the determination component by the analysis unit 32, is not limited thereto. For example, when the components, among the plurality of components, indicating a component waveform that has correlation with the brain resting time and the brain activated time are already identified by previous experiments or the like, the analysis unit 32 may extract these identified components from the plurality of components as the determination components. Additionally, with this brain activity visualization device, in cases where human behavior, which is known to be related to the activation/resting of the brain such as eye movement and blinking are detected, the analysis unit 32 may extract the determination components from the plurality of components by comparing and analyzing the detection results against the component waveform of each component and conducting an evaluation. Note that the criterion for the analysis unit 32 to determine whether or not the first condition is satisfied is appropriately decided by simulations, experiments, theoretical calculations, or the like, in accordance with the purpose of use of the brain activity visualization device 10 or the like.

The second condition is that there is a temperature change at the predetermined site on the human facial surface in the extracted determination components. The analysis unit 32 determines that, among the determination components, the components that satisfy the second condition have a high potential of being related to human brain activity, and extracts these as candidate components. That is, the analysis unit 32 determines whether or not the determination components are related to human brain activity on the basis of the presence/absence of a temperature change at the predetermined site on a human facial surface. Specifically, the analysis unit 32 determines whether or not temperature change has occurred at the forehead and/or the area around the paranasal sinuses on the basis of the temperature distribution data of the extracted determination components. When a temperature change has occurred, the analysis unit 32 determines that there is a high possibility that the determination component satisfies the second condition and is related to human brain activity, and extracts that determination component as a candidate component. Meanwhile, when a temperature change has not occurred at the forehead or the area around the paranasal sinuses, the analysis unit 32 determines that the determination component does not satisfy the second condition and is not a component indicating a skin temperature change that reflects human brain activity (step S6). Note that the criterion for the analysis unit 32 to determine whether or not the second condition is satisfied is appropriately decided by simulations, experiments, theoretical calculations, or the like, in accordance with the purpose of use of the brain activity visualization device 10.

Then, the analysis unit 32 identifies the component which is determined to satisfy the second condition in step S5b, as a component indicating a change in skin temperature that reflects brain activity (step S7). That is, the component identified in step S7 as the component indicating a change in skin temperature that reflects brain activity is a component that is present in both the candidate components extracted by decomposing and analyzing the facial skin temperature data based on temperature conversion data by singular value decomposition and the candidate components extracted by decomposing and analyzing the facial skin temperature data based on relative temperature conversion data by singular value decomposition. Note that, in the candidate components for which both analyses do not match are determined that they are not the component indicating a change in skin temperature that reflects brain activity in step S6.

The estimation unit 33 estimates human brain activity on the basis of the component identified by the analysis unit 32 as a component indicating a change in skin temperature that reflects human brain activity. Specifically, the estimation unit 33 estimates an amount of brain activity when acquiring the facial skin temperature data on the basis of the component waveform data of the component identified by the analysis unit 32.

(4-1-1) Modification Example 1A

The brain activity estimation means 30 described above includes the conversion unit 31, and the facial skin temperature data based on relative temperature conversion data is generated by the conversion unit 31. Moreover, the analysis unit 32 uses singular value decomposition to decompose, into a plurality of components, not only the facial skin temperature data based on temperature conversion data acquired by the facial skin temperature acquisition means 20, but also the facial skin temperature data based on relative temperature conversion data, which is from the temperature data that has been converted into relative temperature data. Then, the analysis unit 32 analyzes each of the components.

Instead of this, a configuration in which the brain activity estimation means 30 does not include the conversion unit 31 can be adopted. In this case, the processes for generating the facial skin temperature data based on relative temperature conversion data and analyzing the data from the facial skin temperature data based on relative temperature conversion data can be omitted.

However, in order to accurately identify the component related to human brain activity, it is preferable that the brain activity estimation means 30 include the conversion unit 31, as in the embodiment described above. Moreover, it is preferable that the analysis unit 32 conducts singular value decomposition to decompose, into a plurality of components, not only the facial skin temperature data based on temperature conversion data acquired by the facial skin temperature acquisition means 20, but also the facial skin temperature data based on relative temperature conversion data, which is from the temperature data that has been converted into relative temperature data; and analyzes each of the components.

(4-1-2) Modification Example 1B

The facial skin temperature acquisition means 20 described above is an infrared thermography device capable of acquiring temperature data in a state of non-contact with the subject.

However, the facial skin temperature acquisition means are not particularly limited to an infrared thermography device, provided that the facial skin temperature acquisition means are capable of detecting the skin temperature of at least a portion of the facial surface of the individual, and chronologically acquiring facial skin temperature data including detected temperature data and position data of the detection site.

For example, the facial skin temperature acquisition means may be a device that includes temperature sensors. Specifically, a configuration is possible in which the temperature sensors are applied to predetermined sites on the facial surface of the individual, and the time-series facial skin temperature data is acquired on the basis of temperature data detected by the temperature sensors and the position data of the sites where the temperature sensors are applied. Even in cases where the facial skin temperature data is acquired while the temperature sensors are in contact with the individual, namely the subject, there is no need to treat the temperature sensors prior to application, unlike case in which electroencephalogram electrodes or the like are used. As a result, data can be acquired more easily compared to conventional detection methods such as electroencephalography, functional magnetic resonance imaging, and near infrared spectroscopy. As such, human brain activity can be easily estimated.

Figure 21:
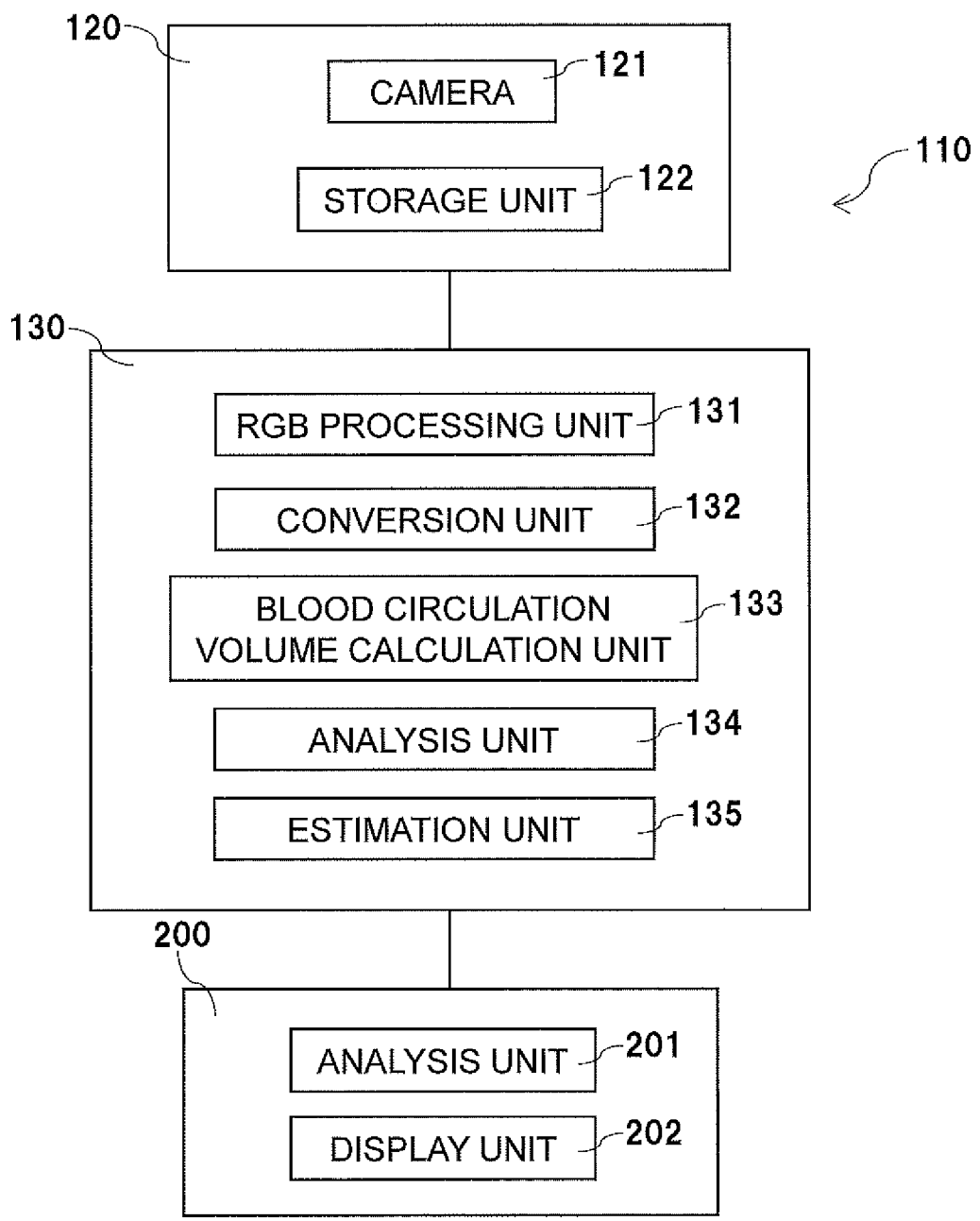
FIG. 21 is a schematic drawing of a brain activity visualization device according to an embodiment of the present invention.
Figure 22:
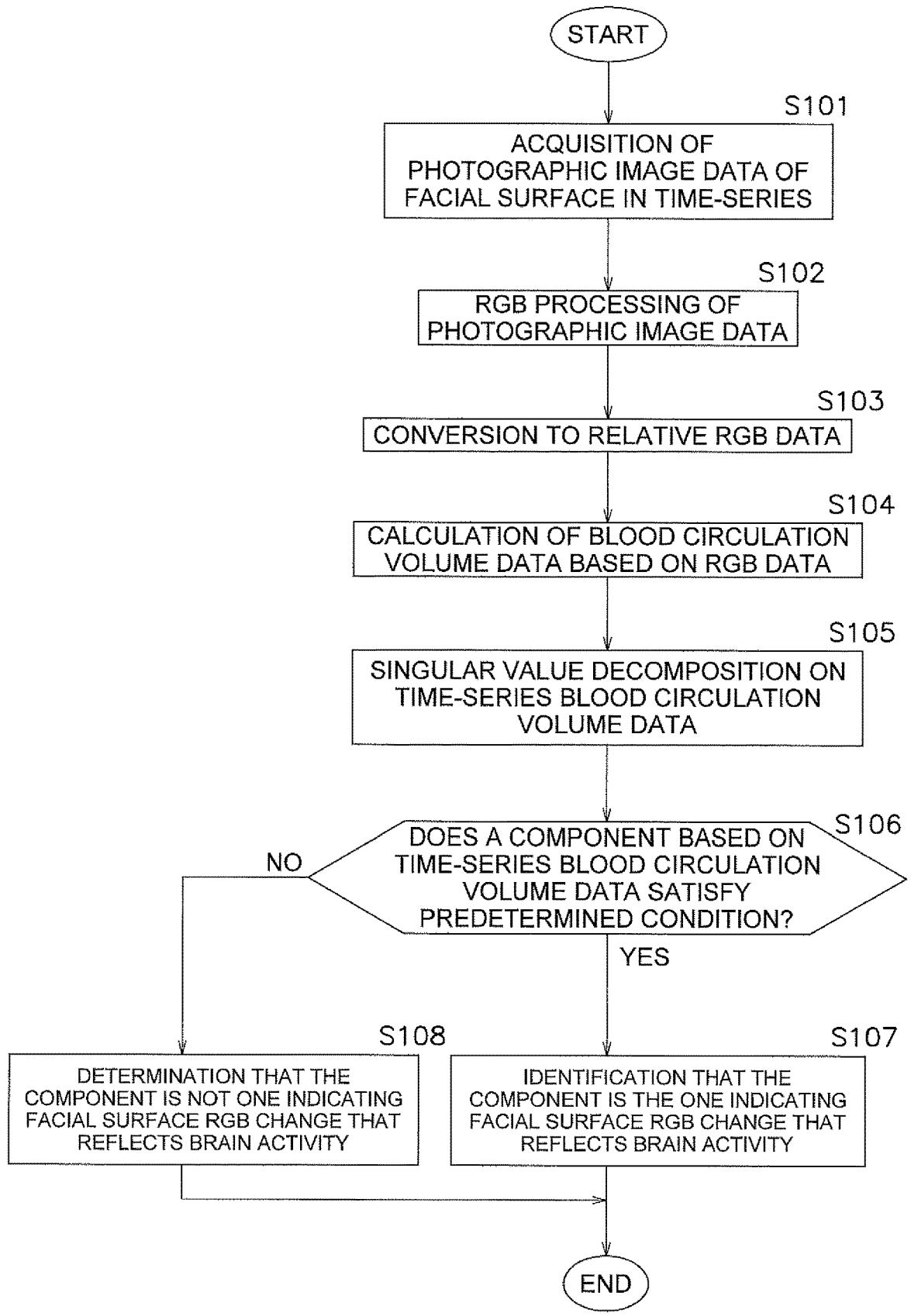
FIG. 22 is a flowchart showing an example of the flow of processing conducted in the brain activity visualization device to identify a component indicating an RGB change in the facial surface that reflects brain function.

(4-2) Brain Activity Estimation Means 130 that Estimate Brain Activity on the Basis of Photographic Image Data of Facial Surface FIG. 21 is a schematic drawing of the brain activity visualization device 110 according to the embodiment of the present invention. FIG. 22 is a flowchart showing an example of the flow of processing conducted in the brain activity visualization device 110 to identify a component indicating an RGB change in the facial surface that reflects brain function.

The brain activity estimation means 130 of the brain activity visualization device 110 estimate the brain activity of an individual (subject) from the photographic image data of the facial surface of the individual. As illustrated in FIG. 21, the brain activity visualization device 110 includes image data acquisition means 120, brain activity estimation means 130, and state visualization means 200.

The image data acquisition means 120 chronologically acquire photographic image data of at least a portion of the facial surface of the individual (step S101). Note that the image data acquisition means 120 are not particularly limited provided that they at least include an imaging device, and examples thereof include smartphones, tablets (e.g. iPad (registered trademark)), and other portable terminals with built in imaging devices. In this case, as illustrated in FIG. 21, the image data acquisition means 120 include a storage unit 122 and a camera 121 as the imaging device. The camera 121 is configured to chronologically acquire photographic image data of the facial surface of the individual. In this case, the camera 121 captures video of the entire facial surface of the individual and acquires the captured video data. The time-series photographic image data captured by the imaging device is stored in the storage unit 122. In this case, the video data acquired by the camera 121 is stored in the storage unit 122.

Note that, in this case, the camera 121 captures video of the entire facial surface, but the present invention is not limited thereto. For example, a configuration is possible in which the camera 121 captures video including images of at least the forehead and/or the area around the paranasal sinuses of the face.

Additionally, in this case, the brain function activation task is given to the individual for a set period of time while the image data acquisition means 120 are acquiring the time-series photographic image data of the facial surface. That is, the photographic image data acquired by the image data acquisition means 120 contains data for a period in which the brain function activation task is being given to the individual. Note that the brain function activation task given to the individual is not particularly limited provided that the task is presumed to place the brain in an activated state, and the content thereof may be appropriately determined in accordance with the purpose of use of the brain activity visualization device 110.

The brain activity estimation means 130 estimate human brain activity on the basis of the time-series photographic image data on the facial surface acquired by the image data acquisition means 120. Specifically, the brain activity estimation means 130 include an RGB processing unit 131, a conversion unit 132, a blood circulation volume calculation unit 133, an analysis unit 134, and an estimation unit 135 as illustrated in FIG. 21. Note that, in FIG. 21, a configuration is illustrated in which the brain activity estimation means 130 are a single device including the RGB processing unit 131, the conversion unit 132, the blood circulation volume calculation unit 133, the analysis unit 134, and the estimation unit 135. However, the present invention is not limited thereto and configurations are possible in which some or all of the RGB processing unit 131, the conversion unit 132, the blood circulation volume calculation unit 133, the analysis unit 134, and the estimation unit 135 are provided as independent devices. Additionally, in this case, facial blood circulation volume acquisition means are configured from the image data acquisition means 120, the RGB processing unit 131, the conversion unit 132, and the blood circulation volume calculation unit 133.

The RGB processing unit 131 performs RGB processing on the photographic image data acquired by the image data acquisition means 120 to decompose the photographic image data into three color components, namely an R component, a G component, and a B component (step S102). The RGB processing may be performed on the photographic image data of the entire facial surface but, in this case, the data of the forehead and/or area around the paranasal sinuses is extracted from the photographic image data and the RGB processing is performed on the extracted data in order to reduce computation load and noise.

The conversion unit 132 converts RGB data of the photographic image data obtained by the RGB processing to relative RGB data (step S103). Specifically, the conversion unit 132 uses, as a reference, an average of the RGB data obtained from the photographic image data for every predetermined time period (e.g. 30 seconds) to convert the RGB data to relative RGB data.

The blood circulation volume calculation unit 133 calculates time-series blood circulation volume data of the facial surface on the basis of the RGB data of the photographic image data obtained by the RGB processing (step S104).

The analysis unit 134 decomposes the time-series relative conversion blood circulation volume data into a plurality of components by singular value decomposition, principal component analysis, or independent component analysis (step S105). Here, the analysis unit 134 subjects each of the relative conversion blood circulation volume data to singular value decomposition in which the SVD of MATLAB (registered trademark) is used as the analysis tool. Specifically, in the singular value decomposition, for the time-series relative conversion blood circulation volume data, the factor is set to time data per predetermined time period (e.g. 30 seconds), and the measure is set to the relative conversion blood circulation volume data per pixel, as calculated from the relative RGB data at each time period. Then, the time-series relative conversion blood circulation volume data is decomposed into a plurality of components by singular value decomposition and a time distribution, a space distribution, and a singular value representing the magnitude of each component is calculated.

Additionally, the analysis unit 134 determines whether or not each component satisfies predetermined conditions in order to identify a component, from the plurality of components decomposed by the singular value decomposition, indicating an RGB change in the facial surface that reflects brain activity (step S106). The predetermined condition includes conditions such as, for example, that the amplitude of the component waveform of the component decomposed by singular value decomposition has correlation with changes at brain resting time and brain activated time (hereinafter referred to as "first condition"), and/or that there is a blood circulation volume change at a predetermined site on the human facial surface in the component decomposed by the singular value decomposition (hereinafter referred to as "second condition"). One or a plurality of conditions may be set as the predetermined condition determined by the analysis unit 134. In this case, the first condition is set as the predetermined condition.

Then, the analysis unit 134 extracts, from the plurality of components, a component that satisfies the predetermined condition as a determination component. Furthermore, the analysis unit 134 identifies, from the extracted determination components, components that satisfy all of the conditions included in the predetermined condition as components indicating an RGB change in the facial surface that reflects brain activity (step S107). Meanwhile, the analysis unit 134 determines that the components among the plurality of components that do not satisfy one or more of the conditions included in the predetermined condition are not components indicating an RGB change in the facial surface that reflects brain activity (step S108).

In this case, as described above, only one condition is set as the predetermined condition, and the brain function activation task is given to the individual for a set period of time while the time-series photographic image data is being acquired. Therefore, the brain resting time is defined as the period of time in which the brain function activation task is not being given to the individual, and the brain activated time is defined as the period of time in which the brain function activation task is being given to the individual. The analysis unit 134 conducts a comparative analysis of the component waveform of each component against the periods of time in which the brain function activation task is and is not being given. Using the results of this comparative analysis based on the component waveform data, the analysis unit 134 evaluates whether or not there is correlation between the component waveform of each component and each of the brain resting time and the brain activated time. Then, the analysis unit 134 extracts, from the plurality of components, a component evaluated as having correlation as a determination component that satisfies the predetermined condition. The analysis unit 134 identifies this determination component as a component indicating an RGB change in the facial surface that reflects brain activity. Meanwhile, the analysis unit 134 determines that, among the plurality of components, a component evaluated as not having correlation is the component that does not satisfy the predetermined condition, and is not the component indicating an RGB change in the facial surface that reflects human brain activity.

In this case, the brain function activation task is given to the individual for a set period of time while acquiring the time-series photographic image data of the facial surface, and the analysis unit 134 extracts the determination component on the basis thereof. However, the content of the first condition, that is, the means of extracting the determination component by the analysis unit 134, is not limited thereto. For example, when the component, among the plurality of components, indicating the component waveform that has correlation with the brain resting time and the brain activated time is already identified by previous experiments or the like, the analysis unit 134 extracts this identified component from the plurality of components as the determination component. Additionally, with the brain activity visualization device 110, in cases where human behavior, which is known to be related to the activation/resting of the brain such as eye movement and blinking are detected, the analysis unit 134 may extract the determination component from the plurality of components by comparing and analyzing these detection results against the component waveform of each component and conducting an evaluation. Note that the criterion for the analysis unit 134 to determine whether or not the first condition is satisfied is appropriately decided by simulations, experiments, theoretical calculations, or the like, in accordance with the purpose of use of the brain activity visualization device 110 or the like.

Additionally, in cases where the second condition is set as the predetermined condition, the analysis unit 134 extracts the determination component on the basis of the presence/absence of a change in facial blood circulation volume at the predetermined site on the human facial surface. Specifically, the analysis unit 134 determines whether or not a change in the blood circulation volume has occurred at the forehead and/or the area around the paranasal sinuses, on the basis of the blood circulation volume distribution diagrams corresponding to the plurality of components decomposed by singular value decomposition. When a change in the blood circulation volume has occurred, the analysis unit 32 determines that said component satisfies the second condition. Meanwhile, when a change in the blood circulation volume has not occurred at the forehead or the area around the paranasal sinuses, the analysis unit 32 determines that said component does not satisfy the second condition. Note that the criterion for the analysis unit 134 to determine whether or not the second condition is satisfied is appropriately determined by simulations, experiments, theoretical calculations, or the like, in accordance with the purpose of use of the brain activity visualization device 110 or the like.

Furthermore, in cases where the blood circulation volume calculation unit 133 calculates the time-series blood circulation volume data based on the RGB data prior to being converted to the relative RGB data, a configuration is possible in which the analysis unit 134 determines whether or not the first condition and/or the second condition is satisfied and extracts a determination component from the plurality of components obtained by subjecting the blood circulation volume data to singular value decomposition or the like.

The estimation unit 135 estimates human brain activity on the basis of the component identified by the analysis unit 134 as a component indicating an RGB change in the facial surface that reflects human brain activity. Specifically, the estimation unit 135 estimates an amount of brain activity when acquiring the photographic image data of the facial surface, on the basis of the component waveform data of the component identified by the analysis unit 134.

(4-2-1) Modification Example 2A

As described above, smartphones, tablets (e.g. iPad (registered trademark)), and other portable terminals with built in imaging devices may be used as the camera 121. In other words, any device that captures images in the visible light region can be used for the photographic image data described above.

Additionally, in the blood circulation volume calculation unit 133, the blood circulation volume data of the facial surface may be calculated using mainly the R component of each pixel included in the RGB data. Provided that the blood circulation volume data can be calculated on the basis of the RGB data, the blood circulation volume data need not be limited to the erythema index.

(4-2-2) Modification Example 2B

The blood circulation volume calculation unit 133 described above calculates the relative conversion blood circulation volume data on the basis of relative RGB data converted by the conversion unit 132. However, in place of or in addition to this, the blood circulation volume calculation unit 133 may calculate the blood circulation volume data on the basis of RGB data prior to being converted to relative RGB data. Components having correlation with brain activity are more likely to be identified (statistical power is high) in blood circulation volume data calculated on the basis of RGB data prior to being converted to relative RGB data. As such, the blood circulation volume data calculated on the basis of RGB data prior to being converted to relative RGB data may be analyzed prior to the relative conversion blood circulation volume data calculated on the basis of relative RGB data. Additionally, a configuration is possible in which the blood circulation volume data is analyzed and components having significant correlation are extracted first and, then, only the components of the relative conversion blood circulation volume data that correspond to the extracted components are analyzed. In this case, computation load can be reduced.

(4-2-3) Modification Example 2C

In the description given above, the camera 121 was assumed to be a typical visible light range camera, but an infrared camera may also be used. In such cases, the infrared camera captures images by emitting infrared light and capturing the reflected waves thereof. The photographic image data of changes in the facial surface of the subject may be obtained in this manner. The present inventors found that there is correlation between the blood circulation volume data calculated from the photographic image data obtained from the reflection of the infrared light and the blood circulation volume data calculated using mainly the R component of each pixel included in the RGB data captured in the visible light region. Accordingly, it is also possible to estimate human brain activity using photographic image data obtained from the reflection of such infrared light.

(4-2-4) Modification Example 2D

Although in the above-mentioned description the brain activity visualization device 110 includes the image data acquisition means 120 and the brain activity estimation means 130, the brain activity visualization device according to the present embodiment is not limited to such a configuration. That is, the brain activity visualization device according to the present embodiment may have any configuration, as long as it includes the blood circulation volume calculation unit 133, the analysis unit 134, and the estimation unit 135. Specifically, the brain activity visualization device according to the present embodiment may take a form, including not only a form in which the device itself generates the image data by photographing, but also a form in which photographic image data is received from an external device to analyze it therein.

(4-3) State Visualization Means 200

The state visualization means 200 display and visualize the physiological state of the subject on the basis of the brain activity of the subject estimated by the brain activity estimation means 30 and/or the brain activity estimation means 130. In one example, the state visualization means 200 may include an analysis unit 201 that analyzes changes in the amount of brain activity of the subject in order to analyze the physiological state of the subject. Specifically, the analysis unit 201 determines the physiological state of the subject by analyzing changes in the amount of brain activity in response to stimulation (e.g. visual stimulation, auditory stimulation, tactile stimulation, olfactory stimulation, or taste stimulation) applied to the subject. Note that, the type and level of the physiological state may be appropriately configured in accordance with the use of the brain activity visualization devices 10, 110, on the basis of a degree of rise and/or duration of the amount of brain activity. Moreover, the state visualization means 200 has a display unit 202 that outputs the physiological state of the subject has analyzed by the analysis unit 201. As a result, an administrator can ascertain the physiological state of the subject. The display unit 202 is not particularly limited, as long as it can visualize information related to the analyzed physiological state of the subject to the administrator. Examples thereof include display devices that display images, messages, and the like.

Additionally, in cases where acquiring various types of time-series data using the facial skin temperature acquisition means 20 and/or the image data acquisition means 120 after the analysis units 32, 134 have identified the components that reflect brain activity, the additionally acquired various types of data is decomposed into a plurality of components by singular value decomposition in the brain activity visualization devices 10, 110, and only the identified components are analyzed. As a result, the physiological state of the subject can be ascertained in real time.

There are techniques for acquiring heart rate information, biological information, and so on of the subject from the skin temperature or captured images of the facial surface of the subject. In addition, conventional techniques can be applied to the components obtained by performing the singular value decomposition or the like on the various data obtained from the facial skin temperature acquisition means 20 and/or the image data acquisition means 120. As such, heart rate information, biological information, or the like can be accurately acquired. Accordingly, a configuration is possible in which the analysis unit 32 and/or the analysis unit 134 is provided with a feature for analyzing the plurality of components obtained from the singular value decomposition and acquiring heart rate information, biological information, or the like, and the estimation units 33, 135 of the embodiment described above are provided with features for estimating functions of the sympathetic nervous system/parasympathetic nervous system on the basis of the acquired heart rate information and/or biological information.

(5) Features (5-1)

In the present embodiment, human brain activity is estimated on the basis of the time-series facial skin temperature data and/or facial blood circulation volume data acquired by the facial skin temperature acquisition means 20 and/or the image data acquisition means 120. As such, human brain activity can be estimated without using electroencephalogram electrodes or other sensors that require pretreatment before being applied. Accordingly, human brain activity can be easily estimated and the physiological state of the subject can be visualized on the basis of the estimated brain activity.

(5-2)

In cases where a situation is created in which the human brain is placed in states of activation and rest by actually giving and withholding the brain function activation task while the time-series facial skin temperature data and/or the image data is being acquired, it can be said that there is a high possibility that the component having correlation between the component waveform of each component and the brain activated time and the brain resting time is a component indicating a change in skin temperature and/or blood circulation volume that reflects brain activity.

In the present embodiment, the brain function activation task is given to the individual for a certain period of time while the facial skin temperature acquisition means 20 and/or the image data acquisition means 120 is acquiring the time-series facial skin temperature data and/or the image data. That is, in the present embodiment, the brain function activation task is actually given to and withheld from the individual and, as a result, a situation is created in which the human brain is placed in an activated state and a resting state. Moreover, the various time-series data thusly acquired is decomposed into a plurality of components by the singular value decomposition, each component is evaluated whether there is correlation between the component waveform thereof and the brain activated time and the brain resting time, and a component evaluated as having correlation is extracted from the plurality of components as the determination component. Thus, compared, for example, to a case in which a predetermined component identified in prior experiments or the like is extracted from the plurality of components as the extraction component, the probability of extraction of a component, which is less related to the human brain activity, as an extraction component from the plurality of components, can be reduced.

(5-3)

The brain has a mechanism called the selective brain cooling system whereby the brain is cooled independently of body temperature. The selective brain cooling system is known to discharge heat generated by brain activity using the forehead and the area around the paranasal sinuses. When heat is discharged, a change in the facial skin temperature resulting from brain activity or the facial blood circulation volume that correlates to the facial skin temperature appears at the forehead and/or the area around the paranasal sinuses.

In the present embodiment, various data of the forehead and/or the area around the paranasal sinuses is analyzed and the determination component is extracted. As such, it is possible to accurately extract components related to human brain activity.

(6) Use Examples of Brain Activity Visualization Device

Next, use examples of the brain activity visualization device according to the present invention will be described. For example, the brain activity visualization devices 10, 110 according to the embodiment or the modification examples described above can determine an emotion, a brain age, health, and the like of an examination subject. Moreover, a useful information presentation device can be provided that presents useful information related to an emotional or physical state on the basis of these determination results.

(6-1-1) When Used to Determine Emotion

An example is described of a case in which the brain activity visualization devices 10, 110 according to the embodiment or the modification examples described above are used to determine an emotion of a subject. In one example, the brain activity visualization devices 10, 110 described above are incorporated into an emotion determination device (useful information presentation device) 300 to enable the determination of the emotion of an examination subject.

Figure 23:
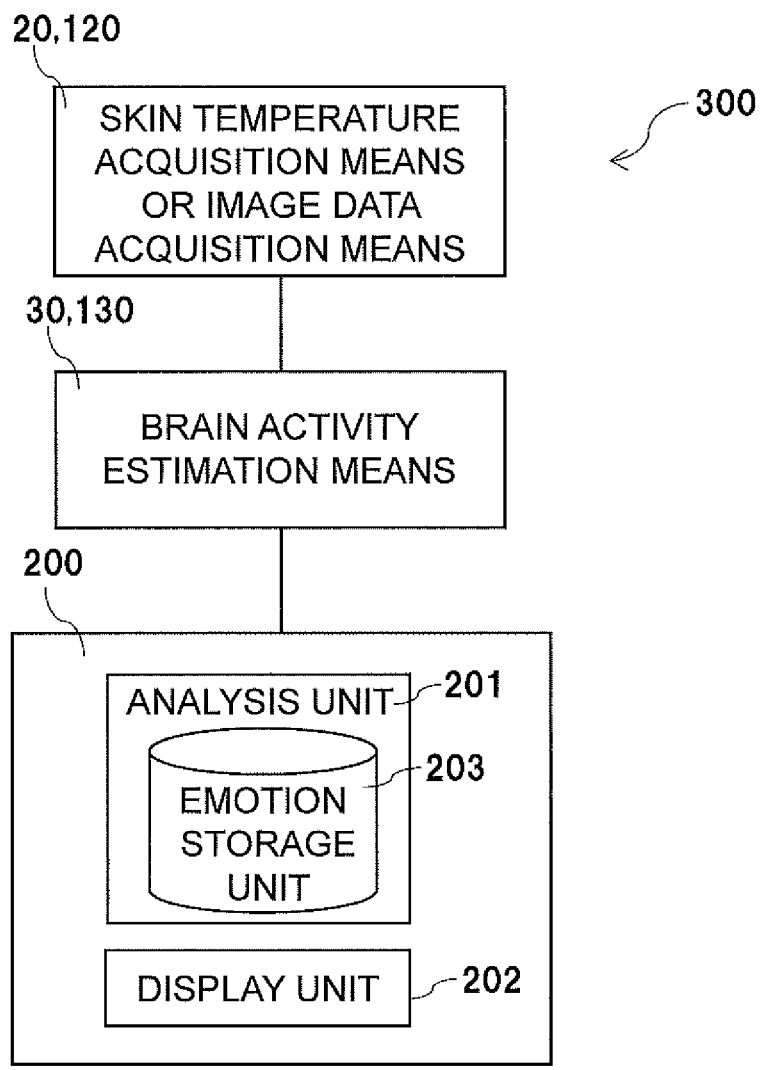
FIG. 23 is a schematic drawing of an emotion determination device (useful information presentation device) according to an embodiment of the present invention.

Specifically, as illustrated in FIG. 23, the state visualization means 200 described above are provided with an emotion storage unit 203. The emotion storage unit 203 is memory in which the estimation results of brain activity and "emotion data" indicating an emotion of a human are associated with one another and stored. Here, the subject is placed in one state of emotion with "joy, anger, pathos, or humor", and then data of the amount of brain activity from when the brain function activation task is given for a certain period of time is collected. The estimation results of brain activity and emotion data emotion are associated with one another on the basis of this data and stored in the emotion storage unit 203. Note that the correlation between the estimation results of brain activity and the emotion data is consecutively optimized.

Moreover, the state visualization means 200 extract the emotion data from the emotion storage unit 203 on the basis of the estimation results of brain activity calculated by the brain activity estimation means 30, 130. As a result, the emotion determination device 300 can present the emotion of the subject on the display unit 202.

To summarize, the emotion determination device 300 includes the facial skin temperature acquisition means 20 and/or the image data acquisition means 120, the brain activity estimation means 30, 130, and the state visualization means (useful information presentation means) 200. The facial skin temperature acquisition means 20 acquire facial skin temperature data in time-series. The image data acquisition means 120 acquire photographic image data of the facial surface in time-series. A plurality of components is obtained by decomposing the facial skin temperature data and/or the facial blood circulation volume data by singular value decomposition, principal component analysis, or independent component analysis. The brain activity estimation means 30, 130 estimate the brain activity of the subject on the basis of this plurality of components. The state visualization means 200 determine the emotion of the subject on the basis of the brain activity of the subject estimated by the brain activity estimation means 30. Accordingly, the emotion determination device 300 can easily determine the emotion of a human or an animal without using electroencephalogram electrodes or other sensors that require pre-treatment before being applied.

(6-1-2) When Used to Determine Emotion of Infant

A configuration is possible in which infant emotion data indicating an emotion of an infant is stored in the emotion storage unit 203. Specifically, a numerical value (rise) of the brain activity of the infant and a degree of a numerical value (high value) of sympathetic nerves are analyzed in advance, and the estimation results of brain activity and the infant emotion data are associated with one another and stored in the emotion storage unit 203. Storing the emotional data specific to infants in the emotion storage unit 203 makes it is possible to determine the emotion of the infant from the estimation results of brain activity. For example, in a state where the infant is crying, it is possible to identify the reason the infant is crying, such as being hungry, being in discomfort due to a diaper issue, or feeling pain.

Typically, infant brain function is undeveloped, but even the emotions of infants can be appropriately determined by using the emotion determination device 300.

(6-1-3) When Used to Determine Emotion of Non-Human Animal

A configuration is possible in which "animal emotion data" indicating an emotion of a non-human animal is stored in the emotion storage unit 203. Storing the emotional data of non-human animals in the emotion storage unit 203 makes it is possible to determine the emotion of those animals. In this case, the facial skin temperature acquisition means 20 or the image data acquisition means 120 acquire information in the best form for the animal. This enables a pet owner to determine whether a companion animal (pet) is comfortable or uncomfortable.

(6-2-1) When Used to Estimate Brain Age

An example is described of a case in which the brain activity visualization devices 10, 110 according to the embodiment or the modification examples described above are used to estimate the brain age of a subject. In one example, the brain activity visualization devices 10, 110 described above are incorporated into a brain age presentation device (useful information presentation device) 301 to enable the determination of the brain age of an examination subject.

Figure 24:
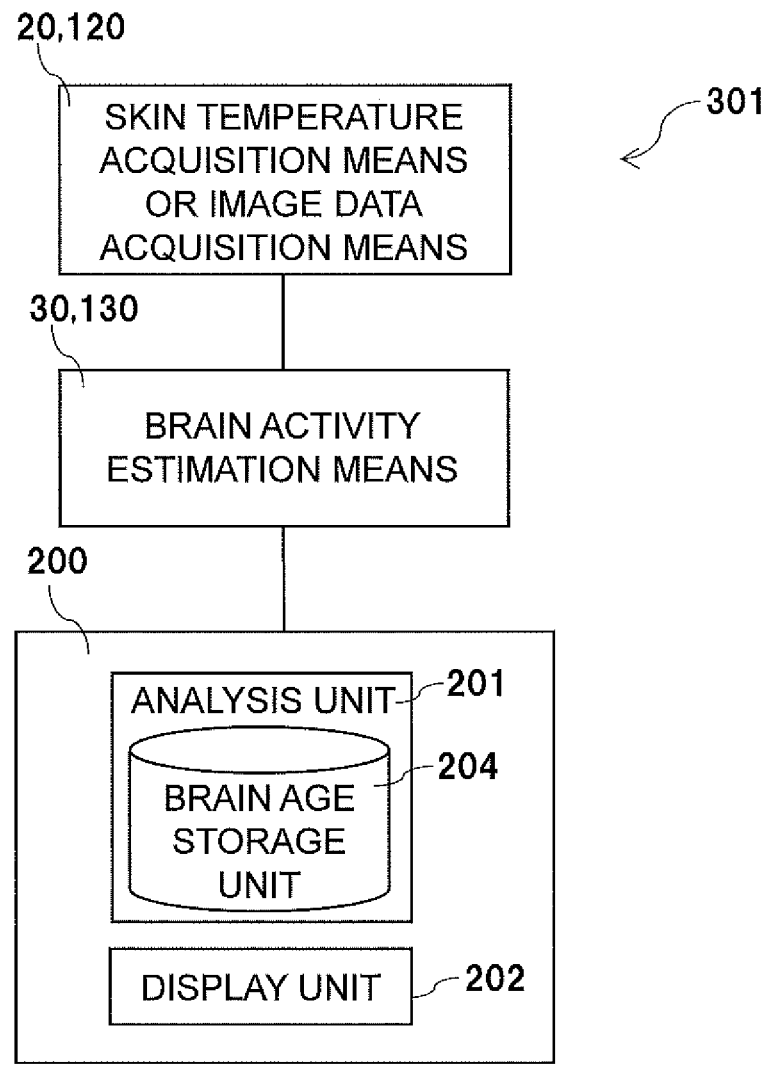
FIG. 24 is a schematic drawing of a brain age presentation device (useful information presentation device) according to an embodiment of the present invention.

Specifically, as illustrated in FIG. 24, the state visualization means 200 described above are provided with a brain age storage unit 204. The brain age storage unit 204 is memory in which the estimation results of brain activity and "brain age data" indicating brain age are associated with one another and stored. In this case, for example, the same brain function activation task is given to a plurality of subjects for a certain period of time, and then data of the amount of brain activity from when the brain function activation task was given is collected. The estimation results of brain activity are classified in accordance with the age of each subject, and the classified estimation results of brain activity and the brain age data are associated with one another and stored in the brain age storage unit 204. Note that the correlation between the estimation results of brain activity and the brain age data indicating brain age is consecutively optimized.

Moreover, the state visualization means 200 extract the brain age data from the brain age storage unit 204 on the basis of the estimation results of brain activity calculated by the brain activity estimation means 30, 130. As a result, the brain age presentation device 301 can present the brain age of the subject on the display unit 202.

To summarize, the brain age presentation device 301 includes the facial skin temperature acquisition means 20 and/or the image data acquisition means 120, the brain activity estimation means 30, 130, and the state visualization means (useful information presentation means) 200. The facial skin temperature acquisition means 20 acquire facial skin temperature data in time-series. The image data acquisition means 120 acquire photographic image data of the facial surface in time-series. A plurality of components is obtained by decomposing the facial skin temperature data and/or the facial blood circulation volume data by singular value decomposition, principal component analysis, or independent component analysis. The brain activity estimation means 30, 130 estimate the brain activity of the subject on the basis of this plurality of components. The state visualization means 200 present the brain age of the subject on the basis of the brain activity of the subject estimated by the brain activity estimation means 30. Accordingly, the brain age presentation device 301 can easily present the brain age without using electroencephalogram electrodes or other sensors that require pretreatment before being applied.

(6-2-2) When Using a Gaming Machine

A configuration is possible in which the brain age presentation device 301 is housed in a gaming machine. Specifically, the facial skin temperature acquisition means 20 and/or the image data acquisition means 120 are installed in a gaming machine. In this case, the facial skin temperature acquisition means 20 and/or the image data acquisition means 120 acquire the facial skin temperature data in time-series and/or the facial surface photographic image data for a predetermined period of time after a game start by the gaming machine. As a result of this configuration, the brain age presentation device 301 can present the brain age during game running Additionally, a configuration is possible in which the game being run by the gaming machine constitutes the brain function activation task. In this case, in accordance with the content of the game, an estimation equation for age and brain activity rise is created in advance on the basis of data collected from a plurality of subjects. Then, each time the game is run, the brain age is estimated on the basis of the estimation equation created for each game. As a result, a message such as "Your brain age is XXX" is presented each time the game is run.

Note that, a configuration is possible in which the brain age presentation device 301 presents diagnosis information for anti-aging, or the like, along with the brain age.

(6-3-1) Advice Related to Health Management

An example is described in which the brain activity visualization devices 10, 110 according to the embodiment or the modification examples described above are applied to a useful information presentation device 302 related to health management.

Figure 25:
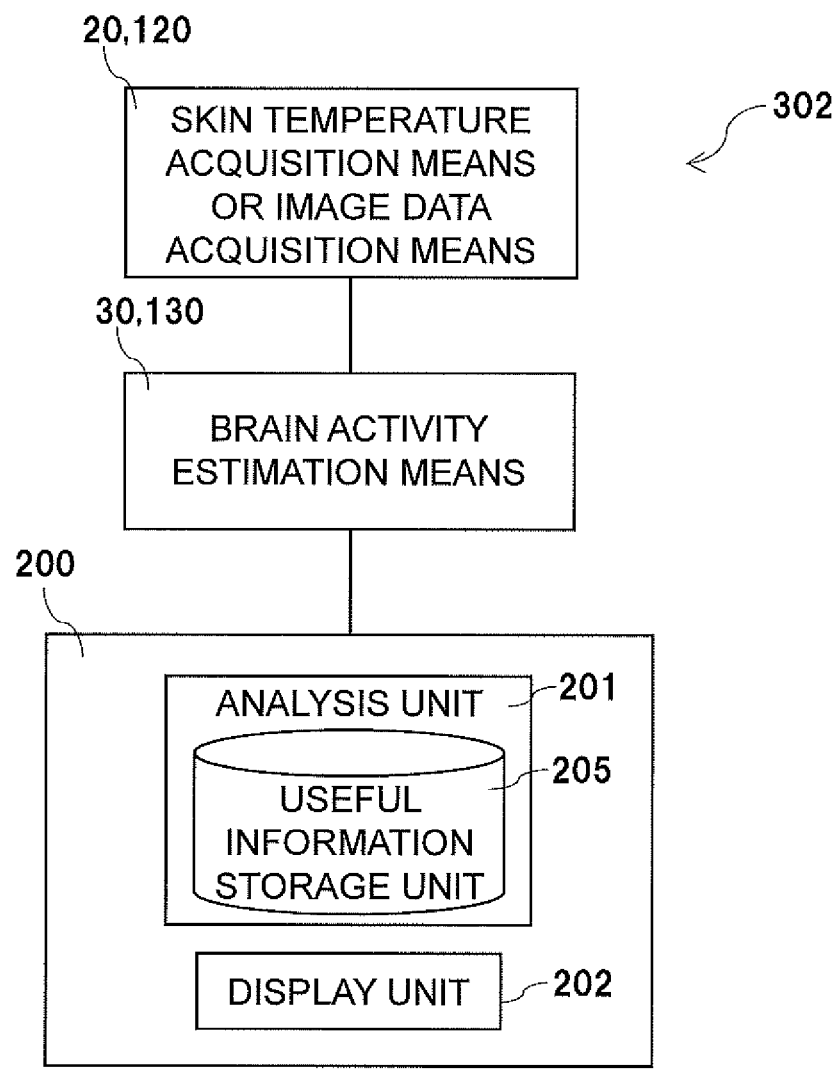
FIG. 25 is a schematic drawing of a useful information presentation device according to an embodiment of the present invention.

Specifically, as illustrated in FIG. 25, the state visualization means 200 described above are provided with a useful information storage unit 205. The useful information storage unit 205 is memory in which the estimation results of brain activity and "useful information" related to health management are associated with one another and stored. In this case, for example, the same brain function activation task is given to a plurality of subjects for a certain period of time, and then data of the amount of brain activity from when the brain function activation task was given is collected. The estimation results of brain activity are classified in accordance with the health condition of the subject, and the classified estimation results of brain activity and the useful information are associated with one another and stored in the useful information storage unit 205. Note that the correlation between the estimation results of brain activity and the useful information is consecutively optimized.

Moreover, the state visualization means 200 extract the useful information from the useful information storage unit 205 on the basis of the estimation results of brain activity calculated by the brain activity estimation means 30, 130. As a result, the useful information presentation device 302 can present useful information related to health management to the subject.

To summarize, the useful information presentation device 302 includes the facial skin temperature acquisition means 20 and/or the image data acquisition means 120, the brain activity estimation means 30, 130, and the state visualization means (useful information presentation means) 200. The facial skin temperature acquisition means 20 acquire facial skin temperature data in time-series. The image data acquisition means 120 acquire photographic image data of the facial surface in time-series. A plurality of components is obtained by decomposing the facial skin temperature data and/or the facial blood circulation volume data by singular value decomposition, principal component analysis, or independent component analysis. The brain activity estimation means 30, 130 estimate the brain activity of the subject on the basis of this plurality of components. The state visualization means 200 present the useful information related to health management to the subject on the basis of the brain activity of the subject estimated by the brain activity estimation means 30. Accordingly, the useful information presentation device 302 can easily present the useful information without using electroencephalogram electrodes or other sensors that require pretreatment before being applied.

(6-3-2) Advice based on Comparison with Circadian Rhythm

As illustrated in FIG. 26, a configuration is possible in which changes by time frame in the estimation results of brain activity are associated with the useful information and stored in the useful information storage unit 205. In this case, the phrase "changes by time frame in the estimation results of brain activity" refers to changes classified into a plurality of patterns on the basis of a value of the estimation results of brain activity and a rate of change in, for example, morning, afternoon, and night time frames. In the example illustrated in FIG. 26, various patterns are set as the changes by time frame in the estimation results of brain activity. In the example illustrated in FIG. 26, a state where "brain activity is low in the morning, the amount of brain activity rises as morning transitions to afternoon, and the amount of brain activity decreases as afternoon transitions to evening" is set as Pattern No. 1; a state where "brain activity is high from the morning and the amount of brain activity is constant until night" is set as Pattern No. 2; and a state where "the amount of brain activity is constant at a low level of brain activity" is set as Pattern No. 3 as the changes by time frame in the estimation results of brain activity. Useful information corresponding to each of these categorized patterns is stored in the useful information storage unit 205. In the example illustrated in FIG. 26, useful information is associated with each of the Pattern Nos. 1 to 3 and stored in the useful information storage unit 205. Specifically, content communicating "Normal: Rhythm is maintained by your lifestyle" is associated with Pattern No. 1; "Abnormal: Overwork, etc. has resulted in a state of excitement. Get some sleep or take a break and let your body rest." is associated with Pattern No. 2; and "Abnormal: Physical activity has decreased and you are in a slump. Become physically active through light exercise, going outside, etc." is associated with Pattern No. 3.

Moreover, with the useful information presentation device 302, the facial skin temperature acquisition means 20 and/or the image data acquisition means 120 acquire the facial skin temperature data and/or the facial surface photographic image data in association with time information. The brain activity estimation means 30, 130 calculate the estimation results of brain activity in association with the time information. Then, the state visualization means 200 extract, from the useful information storage unit 205, useful information in accordance with the changes by time frame in the estimation results of brain activity on the basis of the estimation results and the time information, and present the useful information to the subject. At this time, the state visualization means 200 reference prior estimation results of brain activity and find the pattern of the changes in the estimation results of brain activity in a predetermined period of time. Then, the state visualization means 200 extract the useful information corresponding to that pattern from the useful information storage unit 24.

To summarize, with the useful information presentation device 302 having the configuration described above, it is possible to estimate the balance of the autonomic nervous system, that is, it is possible to estimate whether or not sympathetic nervous system activity and parasympathetic nervous system activity are excessively biased, on the basis of the changes in the estimation results of brain activity during the predetermined period of time. As such, optimal useful information can be presented on the basis of that estimation. In other words, it is possible to present advice based on a comparison with a circadian rhythm.

Note that a configuration is possible in which the useful information presentation device 302 presents the useful information not solely on the basis of the estimation results of brain activity, but on the basis of a combination of the estimation results of brain activity and the change in skin temperature. In the example illustrated in FIG. 26, skin temperature changes in accordance with the states described in Pattern Nos 1 to 3. Specifically, the change in skin temperature is "low in the morning, rises during the day, and decreases in the evening" in Pattern No. 1; the change in skin temperature is "high to start and does not decrease, even in the evening" in Pattern No. 2; and the change in skin temperature is "low to start and does not rise during the day" in Pattern No. 3. Accordingly, by presenting the useful information that corresponds to each of the Pattern Nos. 1 to 3 when the estimation results of brain activity match the Pattern Nos. 1 to 3 and, in addition, the change in skin temperature matches the Pattern Nos. 1 to 3, the validity of the useful information can be enhanced.

(6-3-3) Use of Mirror

With the useful information presentation device 302, a configuration is possible in which the facial skin temperature acquisition means 20 and/or the image data acquisition means 120 are disposed behind a mirror member. With such a configuration, user convenience can be enhanced by, for example, accumulating the estimation results of brain activity each time a user gets dressed using a mirror.

Additionally, a configuration is possible in which the mirror member is a mirrorizing application of a smart device as an embodiment of a mirror member. For example, a camera or the like mounted on the smart device can be used to pseudo-mirrorize a display unit of the smart device. User convenience can be enhanced by disposing the facial skin temperature acquisition means 20 and/or the image data acquisition means 120 behind the display unit of a portable smart device. Here, examples of the smart device include multifunction mobile phones and the like.

(7) Use in Smart Device

A configuration is possible in which the brain activity visualization devices 10, 110 according to the present embodiment are housed in a smart device. Specifically, a configuration is possible in which the facial skin temperature acquisition means 20 and/or the image data acquisition means 120, the brain activity estimation means 30, 130, and the state visualization means 200 are housed in a smart device such as a multifunction mobile phone or the like. Furthermore, when the brain activity visualization devices 10, 110 are used as the useful information presentation device housed in a smart device, it is possible for the user to input and output information and carry out calculations using the smart device carried with the user. As a result, brain age, emotions of people or animals, health management, and other useful information can be easily acquired.

Alternatively, a configuration is possible in which the facial skin temperature acquisition means 20 and/or the image data acquisition means 120, and the state visualization means 200 are housed in a smart device such as a multifunction mobile phone or the like, and the brain activity estimation means 30, 130 are housed in a server device. Such a configuration enables a reduction in the calculation load of the smart device main unit. Additionally, by managing data on a server device, multiple pieces of data can be collected and optimized and, as a result, the accuracy of the output results can be enhanced. For example, the accuracy of the useful information can be enhanced by optimizing the association between the estimation results of brain activity and the useful information in a timely manner. Additionally, the accuracy of the brain age determination can be enhanced by optimizing the association of the estimation results of brain activity with the brain age data of the examination subject in a timely manner. Moreover, the accuracy of the emotion determination can be enhanced by optimizing the association of the estimation results of brain activity with the emotion data of the examination subject in a timely manner.

Additional Description

The present invention is not limited to the embodiments described above. Various modifications may be made to the constituent elements of the present invention at the stage of implementation, without departing from the gist of the present invention. Various types of the invention can be formed by appropriately combining a plurality of the constituent elements disclosed in the foregoing embodiments. Some of the elements, for example, may be omitted from the whole of the constituent elements shown in the embodiments mentioned above. Furthermore, the constituent elements over different embodiments may be appropriately combined.

INDUSTRIAL APPLICABILITY

The present invention can easily estimate brain activity and, as such, is useful for applications to brain activity visualization devices that visualize the physiological state of subjects on the basis of their brain activity.

What is claimed is:

1. A useful information presentation device comprising:
at least one of an imaging device and a plurality of temperature sensors;
a processor communicatively connected to the at least one of the imaging device and the plurality of temperature sensors; and
a display device communicatively connected to the processor,
the processor being configured to execute at least one of acquiring facial skin temperature data including skin temperature data detected from a facial surface of a subject based on image data captured by the imaging device or temperature data detected by the plurality of temperature sensors in a time series, and acquiring position data of a detection site of the facial skin temperature data in time-series, and
obtaining photographic image data of the facial surface of the subject from the imaging device in time-series, obtaining RGB data of the photographic image data by subjecting the photographic image data to RGB processing, and acquiring facial blood circulation volume data based on the RGB data in time-series,
the processor being further configured to
decompose at least one of the facial skin temperature data and the facial blood circulation volume data into a plurality of components by singular value decomposition, principal component analysis, or independent component analysis, and estimate brain activity of the subject based on the plurality of components; and
control the display device to present to the subject useful information related to an emotional or physical state based on the estimated brain activity of the subject
at least a portion the facial skin temperature data and/or the facial blood circulation volume data are obtained from a region around paranasal sinuses and/or a forehead of the subject.

2. The useful information presentation device according to claim 1, wherein
the processor is further configured to
extract, from the plurality of components, a component having a waveform with an amplitude that has correlation with changes of a brain resting time and a brain activated time as a determination component, and
estimate the brain activity of the subject based on the determination component.

3. The useful information presentation device according to claim 1, wherein
the at least one of the plurality of temperature sensors and the imaging device includes the imaging device, and
the imaging device and the display device are housed in a smart device.

4. The useful information presentation device according to claim 3, wherein
the smart device includes a mirror member that mirrorizes the display device,
the at least one of the plurality of temperature sensors and the imaging device includes the imaging device, and
the imaging device is disposed behind the display device.

5. The useful information presentation device according to claim 1, wherein
the at least one of the plurality of temperature sensors and the imaging device includes the imaging device, and
the imaging device, the processor, and the display device are housed in a smart device.

6. The useful information presentation device according to claim 5, wherein
the at least one of the plurality of temperature sensors and the imaging device includes the imaging device, and
the imaging device is installed in a gaming machine that acquires at least one of the facial skin temperature data and the facial blood circulation volume data in time-series for a predetermined period of time after a game start by the gaming machine.

7. The useful information presentation device according to claim 1, further comprising:
an emotion storage unit that stores estimation results of brain activity and emotion data indicating an emotion of a human in association with each other,
the processor calculating the estimation results of brain activity, extracting emotional data of the subject based on the estimation results from the emotion storage unit, and presenting the emotional data on the display device.

8. The useful information presentation device according to claim 7, wherein,
the emotion storage unit stores infant emotion data indicating an emotion of an infant and associates the infant emotion data with estimation values of brain activity, and
the processor is configured to determine the emotion of the infant based on the estimated brain activity and the infant emotion data.

9. The useful information presentation device according to claim 7, wherein
the useful information presentation device is configured to determine an emotion of a non-human animal instead of a human.

10. The useful information presentation device according to claim 1, further comprising:
a brain age storage unit that associates and stores brain age data indicating a brain age and associates the brain age data with estimation results of brain activity,
the processor calculating the estimation results of brain activity, extracting brain age data of the subject from the brain age storage unit based on the estimation results, and presenting the brain age data on the display device.

11. The useful information presentation device according to claim 1, further comprising:
a useful information storage unit that stores the useful information related to health management in association with estimation results of brain activity,
the processor calculating the estimation results of brain activity, extracting useful information for the subject based on the estimation results from the useful information storage unit, and presenting the useful information on the display device.

12. The useful information presentation device according to claim 11, wherein
- the useful information storage unit stores the useful information in association with changes by time frame in the estimation results of brain activity,
- the at least one of the plurality of temperature sensors and the imaging device is configured to acquire at least one of the facial skin temperature data and the facial blood circulation volume data in association with time information,
- the brain activity estimation unit calculates the estimation results of brain activity in association with the time information, and
- the useful information presentation unit extracts, from the useful information storage unit, the useful information in accordance with the changes by time frame in the estimation results of brain activity based on the estimation results and the time information, and presents the useful information to the subject.

13. The useful information presentation device according to claim 1, wherein
- the at least one of the plurality of temperature sensors and the imaging device includes the imaging device, and
- the imaging device is disposed behind a mirror member.

* * * * *